US012734304B2

(12) United States Patent
Plumptre et al.

(10) Patent No.: US 12,734,304 B2
(45) Date of Patent: Sep. 15, 2026

(54) MODULAR SYSTEM FOR A DRUG DELIVERY DEVICE WITH ELECTRONIC AND CORRESPONDING MODULES AND METHOD

(71) Applicant: Sanofi, Paris (FR)

(72) Inventors: David Aubrey Plumptre, Warwick (GB); Oliver Charles Gazeley, Warwick (GB); Robert Veasey, Warwick (GB); Michael Jugl, Frankfurt am Main (DE); Stefan Blancke, Frankfurt am Main (DE)

(73) Assignee: Sanofi, Paris (FR)

(*) Notice: Subject to any disclaimer, the term of this patent is extended or adjusted under 35 U.S.C. 154(b) by 1140 days.

(21) Appl. No.: 17/782,482

(22) PCT Filed: Dec. 11, 2020

(86) PCT No.: PCT/EP2020/085728

§ 371 (c)(1),
(2) Date: Jun. 3, 2022

(87) PCT Pub. No.: WO2021/116387

PCT Pub. Date: Jun. 17, 2021

(65) Prior Publication Data

US 2023/0030744 A1 Feb. 2, 2023

(30) Foreign Application Priority Data

Dec. 11, 2019 (EP) .................................... 19306630

(51) Int. Cl.
*A61M 5/315* (2006.01)

(52) U.S. Cl.
CPC . *A61M 5/31568* (2013.01); *A61M 2205/0216* (2013.01); *A61M 2205/0238* (2013.01); *A61M 2205/3306* (2013.01); *A61M 2205/50* (2013.01); *A61M 2207/10* (2013.01)

(58) Field of Classification Search
CPC .......... A61M 5/31568; A61M 5/31566; A61M 5/31565; A61M 5/31573; A61M 5/31546;
(Continued)

(56) References Cited

U.S. PATENT DOCUMENTS

2003/0173507 A1 9/2003 Paritsky et al.
2007/0228516 A1 10/2007 Plank et al.
(Continued)

FOREIGN PATENT DOCUMENTS

CN 108353511 A 7/2018
CN 108430877 A 8/2018
(Continued)

OTHER PUBLICATIONS

International Preliminary Report on Patentability in International Appln. No. PCT/EP2020/085728, mailed on Jun. 23, 2022, 10 pages.

(Continued)

*Primary Examiner* — Tasnim Mehjabin Ahmed
(74) *Attorney, Agent, or Firm* — Fish & Richardson P.C.

(57) ABSTRACT

Disclosed is a modular system for a drug delivery device with electronic, comprising a mechanical module that comprises a distal end and a proximal end, and a mechanism that is configured to set and/or to deliver a dose of the drug out of the distal end (D) of the mechanical module, an electronic module that comprises a detector unit, and an electronic unit that is operatively coupled to the detector unit, wherein the electronic module is removably mechanically coupled or coupleable to the mechanical module in a proximal end region of the mechanical module.

22 Claims, 4 Drawing Sheets

(58) Field of Classification Search
CPC ...... A61M 5/31545; A61M 2205/0216; A61M 2205/0238; A61M 2205/3306; A61M 2205/50; A61M 2207/10; H01L 2924/181
See application file for complete search history.

(56) References Cited

U.S. PATENT DOCUMENTS

| | | | | |
|---|---|---|---|---|
| 2012/0112235 | A1 | 5/2012 | Preuschl et al. | |
| 2014/0151868 | A1 | 6/2014 | Bayerer | |
| 2018/0318497 | A1 | 11/2018 | Sluggett et al. | |
| 2018/0352666 | A1* | 12/2018 | Liskow | H05K 3/368 |
| 2020/0171246 | A1* | 6/2020 | Byerly | A61M 5/20 |
| 2020/0330005 | A1 | 10/2020 | Barry et al. | |

FOREIGN PATENT DOCUMENTS

| | | | |
|---|---|---|---|
| DE | 102009032424 | A1 | 1/2011 |
| EP | 3329842 | | 6/2018 |
| EP | 2988801 | | 2/2019 |
| JP | 2012-006419 | A | 1/2012 |
| JP | 2013-069780 | A | 4/2013 |
| WO | WO 2011/117282 | A1 | 9/2011 |
| WO | WO 2012/046199 | | 4/2012 |
| WO | WO 2013/004844 | A1 | 1/2013 |
| WO | WO 2017/118681 | A1 | 7/2017 |
| WO | WO 2018/013843 | | 1/2018 |
| WO | WO 2019/036576 | | 2/2019 |
| WO | WO 2019/101962 | A1 | 5/2019 |
| WO | WO 2021/214275 | A1 | 10/2021 |

OTHER PUBLICATIONS

International Search Report and Written Opinion in International Appln. No. PCT/EP2020/085728, mailed on Mar. 12, 2021, 13 pages.

* cited by examiner

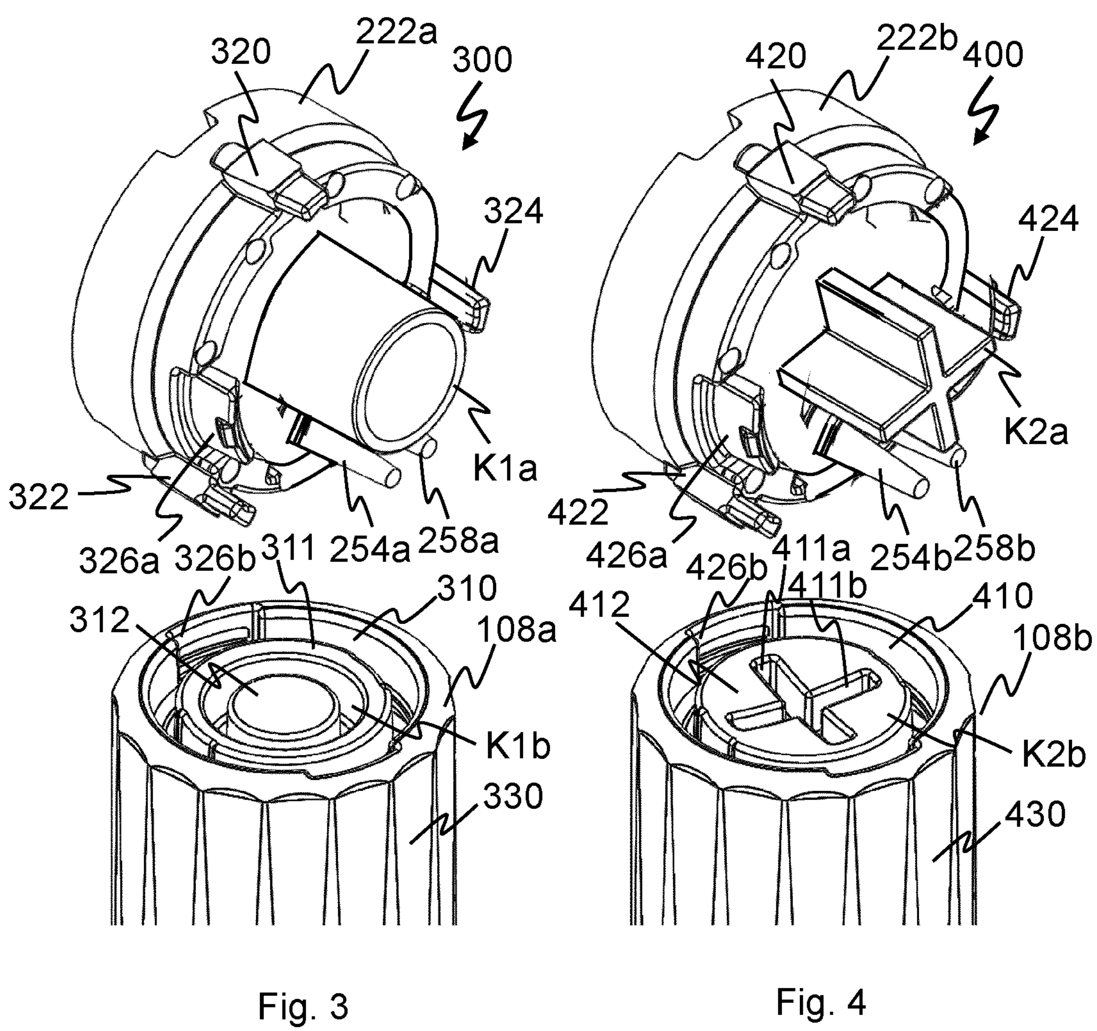
Fig. 3
Fig. 4
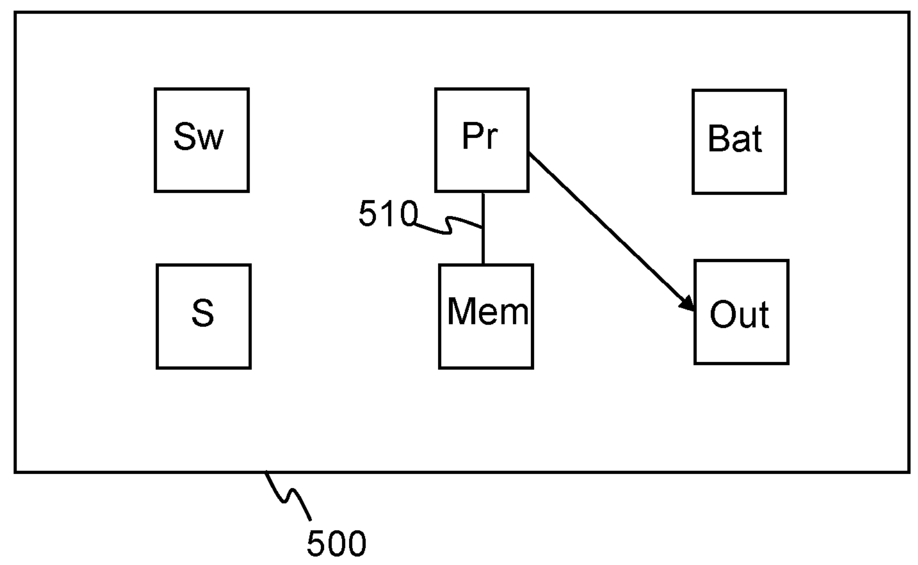
Fig. 5

MODULAR SYSTEM FOR A DRUG DELIVERY DEVICE WITH ELECTRONIC AND CORRESPONDING MODULES AND METHOD

CROSS REFERENCE TO RELATED APPLICATIONS

The present application is the national stage entry of International Patent Application No. PCT/EP2020/085728, filed on Dec. 11, 2020, and claims priority to Application No. EP 19306630.5, filed on Dec. 11, 2019, the disclosures of which are incorporated herein by reference.

TECHNICAL FIELD

The disclosure relates to a modular system of a drug delivery device with electronic and to corresponding modules. The drug delivery device may be an autoinjector or a manually or semi-automatically operated device. An energy-storing element may be used in autoinjectors as well as in semi-automatically operated devices in order to deliver the driving force for the injection operation. The energy-storing element may be biased in the factory or by the user prior to use. The drug may comprise insulin or GLP-1 (Glucagon-Like Peptide). However, other drugs may also be injected. Furthermore, other medical devices may also profit from the disclosure, e.g., injectors, spraying devices, or inhalation devices.

BACKGROUND

Usually, drug delivery devices may comprise a lot of mechanical components. However, there may be the desire to use electronic components together with mechanical components. A modular system would allow multi use of the electronic component. However, it might be cumbersome to attach an electronic module for instance laterally to a drug delivery device.

SUMMARY

It is an object of the disclosure to provide a modular system of a drug delivery device. The modular system should be preferably easily and/or comfortably to use. The modular system should preferably be small in size and/or should allow the usage of drug delivery devices that are known without modification or with only slight modifications. Preferably, electronic and electro-mechanical components of the modular system should be protected in a simple and easy way against environmental ingress, e.g., dust, humidity, mechanical manipulation, etc. Furthermore, corresponding modules shall be given. A corresponding method of using and a method of manufacturing should also be provided.

The proposed modular system for a drug delivery device with electronic, may comprise:

- a mechanical module that comprises:
  - a distal end and a proximal end, and
  - a mechanism that may be configured to set and/or to deliver a dose of the drug out of the distal end of the mechanical module, and
- an electronic module that comprises:
  - a detector unit, and
  - an electronic unit that may be operatively, e.g., electrically (for instance by wire or via RF (radio frequency), coupled to the detector unit.

The proposed modular system for a drug delivery device with electronic, may comprise:

- a mechanical module that comprises:
  - a distal end and a proximal end, and
  - a mechanism that may be configured to set and/or to deliver a dose of the drug out of the distal end of the mechanical module, and
- an electronic module that comprises:
  - a detector unit, and
  - an electronic unit that may be operatively, e.g., electrically (for instance by wire or via RF (radio frequency), coupled to the detector unit.

The electronic module may be mechanically coupled or may be coupleable to the mechanical module in a proximal end region of the mechanical module. The mechanical module and the electronic module may be removable coupled/connected or may be coupleable/connectable to each other.

The technical effect of a proximal coupling of the electronic module to the mechanical module is that the length of the drug delivery device is prolonged only slightly whereby the width or diameter of the drug delivery device is not changed. Thus, a comfortable pen shape is remained that allows high user comfort and easy handling. Nevertheless, the electronic module may be used with several drug delivery devices because the modular system is only a temporary assembly.

A clip connection or another connection may be used to connect the mechanical module and the electronic module. No electronic connection may be necessary between the mechanical module and the electronic module thus simplifying the interface, i.e., only a mechanical interface may be necessary but no electrical interface.

The mechanical connection may be released without usage of a further tool. Alternatively, a special tool may be used to ease separation and/or connection of both modules, especially for elderly person and/or for persons with reduced dexterity. Independent of the usage of a tool or not, both modules may be removable/releasable without destroying parts and/or with using only one, two, three or four hand movements, e.g., disassembling of both modules may be possible within 30 seconds.

The detection unit may detect the amount of the drug to be delivered during setting of the dose. Alternatively or additionally, the detection unit may detect the amount of the delivered drug during the injection of the drug.

The detection may be based on the detection of rotation or of relative rotation between mechanical parts of the mechanism or between such parts and the detection unit. Alternatively or additionally, translation or relative translation may be detected between parts of the mechanism or between such parts and the detection unit.

The detection unit may comprise at least one sensor. The at least one sensor may work on one or on several physical principles of a wide range of physical principles. For example, an optical sensor, an electromechanical sensor, a magnetic sensor (hall sensor), a capacitive sensor, an inductivity sensor, an ultrasound sensor and/or a pressure sensor may be used within the detection unit.

The mechanical module may comprise many components of a drug delivery device:

- a plunger rod element that may press on a plunger within a syringe or cartridge of the drug delivery device in order to expel the drug, and/or
- optionally, a drive mechanism comprising an energy storing element, for instance a mechanical spring, and/or optionally a syringe or cartridge, preferably a changeable syringe or cartridge, or a pre filled container that is part of the mechanical module, and/or optionally a number sleeve with numbers indicating amounts of drug to be delivered. The number sleeve may be rotatable and/or axially movable along central axis of number sleeve by rotating a dial sleeve or dial element.

The electronic module may comprise:

a battery or rechargeable accumulator holder, and/or optionally a battery or a rechargeable accumulator, and/or optionally only one or at least one circuit board, and/or electronic parts, e.g., resistors and/or at least one integrated circuit, may form an electronic circuit or circuitry, the electronic parts may comprise at least one sensor element, for instance an optical sensor, and/or a microprocessor or microcontroller or another control unit, and/or optionally a receiving and/or transmitting (sending) unit, for instance based on the Bluetooth® protocol, the Wi-Fi protocol or on the USB protocol (Universal Serial Bus), for instance for communication with a smartphone or other computer device, and/or an extension for the sensor, for instance a light guide that is for instance attached to a circuit board, and/or at least one switch, for instance for power management.

The distal end of the mechanical module and the proximal end of the mechanical module may be arranged on a longitudinal axis of the mechanical module. The second module may be arranged on the extended longitudinal axis of the mechanical module. Thus, a serial coupling along the longitudinal axis may be realized.

The detector unit may comprise an extension feature or may be arranged on an extension feature that extends from the electronic module distally beyond the proximal end of the mechanical module. Alternatively, the detector unit may have a detection range that extends from the electronic module distally beyond the proximal end of the mechanical module. The extension feature may extend at least 3 mm (millimeter), at least 4 mm or at least 5 mm beyond the proximal end of the mechanical module. The distance may be for instance less than 20 mm. The extension feature may be a light guide or an optical guide. The extension feature may be interdigitated with the proximal end section of the mechanical module. The extension feature may allow to use a mechanical module that has the movable and/or rotatable part that is used for the detection of the selected or delivered drug deeper within the mechanical module. This may give freedoms for design of the mechanical module. Furthermore, purely mechanically drug delivery devices may be used without further modification together with the electronic module.

The mechanical module may comprise a proximal part with at least one aperture. The extension feature may extend into or through the aperture or it may extend to a position near the at least one aperture, for instance to a position that has a distance to the aperture in the range of 0.1 mm (millimeter) to 3 mm. The aperture may be arranged within the casing of the mechanical module. The aperture may be as small as necessary for the detection by the detection unit in order to allow a high protection function of the casing of the mechanical module even if the electrical module is not mounted to the mechanical module.

The proximal part may be a casing or a grip button or an extension/dial sleeve of the mechanical module. The extension/dial sleeve may extend out of the casing of the drug delivery device if the amount of dose is dialed. The extension sleeve may be moved manually back into the inside of the casing of the mechanical module during injection. Alternatively, the user may bias an energy storing element during dialing the amount of the dose. The energy of the energy storing element may be used to inject the selected dose of the drug. There may be the technical effect that the moving part, e.g., an indicator element, of the mechanical module may be reached by an axially extending extension feature in an easy and simple way if the extension feature extends into or through the proximal part of the drug delivery device to a rotating feature.

The detector unit may comprise at least one optical sensor unit and at least one optical source unit. The detector unit may preferably comprise an optical guide unit that is part of the extension feature or that forms the extension feature. An optical sensor may allow detection without making mechanical contact, e.g., without disturbing the movement of rotating and/or linearly moving parts. Furthermore, optical sensors may have only a small radiation impact to the environment and may be operated using little energy thus enabling for instance long operating time of a battery or accumulator.

The extension feature that is used as an optical guide may have a mechanical stable cone shape or a frustum shape, e.g., with a smaller diameter on its free end compared to a diameter on its basis. Additionally or alternatively, the cone shape may ease the insertion of the extension feature into the mechanical module. Alternatively, cylindrically shaped optical guides may be used.

The extension features may be arranged laterally of a longitudinal middle axis of the mechanical module thereby allowing easy detection on a rotating part that may rotate around the middle axis, for instance on rotating parts comprising radially protruding features (teeth, corrugated features, etc.). It may be possible to use only one optical guide for each detection unit, i.e. for forward and backward guiding of the electromagnetic radiation. Alternatively, two optical (light) guides may be used, for instance in order to reduce noise and or to raise the responsivity of the detection unit. The optical guide(s) may comprise a solid guide and/or a hollow pipe.

The optical guide may comprise a border surface that may guide an electromagnetic radiation by total reflection. Thus, the radiation may be reflected without energy losses allowing raising the responsivity of the detection unit. The optical guide may be configured to guide electromagnetic radiation that is radiated from the optical source unit through the optical guide. The optical guide or a further optical guide may be configured to guide at least a part of the electromagnetic radiation back to the optical sensor unit. The electromagnetic radiation that is guided back to the optical sensor unit may be reflected or transmitted radiation, for instance reflected light or transmitted light, e.g., having a wavelength within the range of 400 nm to 700 nm or to 780 nm (visible light) or within the range of 780 nm to 1 mm (infrared light). Reflected radiation may be sensed easier than transmitted radiation, e.g., light. Transmitted radiation may be brighter than reflected radiation using the same radiation source.

The optical guide may be different from a lens that forms the casing of the optical source unit, for instance an LED (Light Emitting Diode) having a transparent casing made of for instance synthetic resin or plastic. There may be an air gap between the casing of the LED and the optical guide.

The at least one optical guide may be laterally coated, e.g., along its complete circumference, with a coating material that is different from a material or from a core material of the at least one optical guide. The coating material may comprise:

- a metal for instance a metal to stiffen up the structure of the light/optical guide/pipe, and/or
- a soft coating material that is softer than the material of the optical guide. The soft coating may be configured to absorb impact loads resulting in less mechanical stress to the light pipe or optical guide, and/or
- a reinforced coating that is reinforced for instance by carbon fibers or by carbon fiber reinforced polymer/plastic.

All three coating materials may prevent that loads, impact, dirt, fluids, e.g., liquids and/or gases, from outside have a detrimental impact on the optical guide, especially to the border surface that is used for total reflection. Combinations of two or all three options of coatings are possible, for instance using two or three different coating layers.

Carbon fiber reinforced polymer/plastic/thermoplastic (CFRP, CRP, CFRTP) may be used which comprises carbon fibers. A binding polymer may be used, for instance a thermoset resin such as epoxy. Other thermoset or thermoplastic polymers may be used as well, for instance polyester, vinyl ester or nylon. The composite material may comprise or contain aramid (Kevlar® or Twaron® in addition to the carbon fibers.

The coating material may be tuned such that the border surface that is used for total reflection is not impaired by the coating itself. The coating may protect the side walls of the extension feature along the complete length or along at least 80 percent of length. On a basis of the extension feature, protection may be given by a cup like structure that surrounds the extension feature, e.g., a light pipe or an optical guide.

The electronic module may comprise a substrate that carries the parts or at least some parts of the electronic unit. Only one side or both sides of the substrate may be covered at least partially or at all locations that are not covered by electronic parts by a potting compound or by a conformal coating layer. A conformal coating or deposition method may be used for producing the conformal coating layer. Conformal may mean that the topography (three-dimensional profile) of the surface is preserved in the coating layer, for instance edges (elongated edges) and corners. Contrary, non-conformal may mean that the topography is not maintained, e.g., if a very viscous potting compound or potting material is used.

A chassis that carries and/or that comprises at least a part of the detector unit may be configured to separate the potting compound from an electrical sensor and/or from a radiation source of the detector unit and/or from the extension feature of the detector unit. Silicone, polyurethane, etc. may be used as a potting material or as a potting compound. The potting material/compound may protect the electronic from environmental influences, e.g., dust or humidity. The potting material/compound may mechanically stabilize the electronic module and/or may enhance or create a connection between different parts of the electronic module.

Several protection measures may be combined, for instance: potting and/or coating of the extension feature and/or blocking/keying features as mentioned below.

The substrate may comprise one or more metallic sheet layers laminated to an insulator or non-conductive substrate, for instance to an FR4 (Fire resist) material that may comprise epoxy and glass fibers or fibers of another material. The substrate may be a one-sided substrate or a two-sided substrate that may reduce the overall dimensions of the substrate. Thus, the substrate may be a printed circuit board.

The electronic module may comprise a protruding element. The protruding element may be configured to block unwanted touching and deliberate touching of the extension feature(s) and/or of other internal parts of the electronic module by a user. Additionally or alternatively, the protruding element may be configured as a keying element that interdigitates with an inverse shaped keying element of the mechanical module. The keying elements may be an annular ring and an annular notch or a crosswise protruding feature and a crosswise groove. However, other appropriate shapes may be used as well, e.g., a prism. There may be two separate protruding elements, e.g., one for blocking and the other for keying.

The protruding keying/blocking feature(s) may extend to the same length as the extension feature, for instance measured relative to a circuit carrier/board or substrate within the electronic module, or within the range of plus 10 or 20 percent relative to the length or distance of a distal end of the extension feature from the substrate of the electronic unit. Thus, the blocking/keying features may mechanically protect the extension feature.

Different keying parts for different drug delivery devices may be used. The electronic modules having different keying features may operate different if compared to each other. The selected and/or injected amount of the drug may be calculated in different ways depending on the type of the electronic unit and of the type of the corresponding, e.g., fitting, drug delivery device.

The mechanical module may comprise a movable and/or rotatable indicator element that is coupled to the mechanism. At least a part of the detector unit may be arranged at the indicator element. The detector unit may be configured to detect the movement (translation and/or rotation) of the movable and/or rotatable indicator element to determine the size of the dose of the drug to be delivered (e.g., size or amount of dose is detected during dose setting) or delivered (e.g., size or amount of dose is detected during dose delivery) by the mechanism during a dose delivery operation. The indicator element may comprise a corrugated or castellated surface and/or areas of different absorption or reflectivity for optical radiation. The detection of a rotation and/or translation of the indicator element/indicator surface may be much simpler using protruding features, e.g., tooth of a clutch sprocket or of a clutch sprocket sleeve.

The mechanical module may comprise a proximal button, preferably a button comprising an outer knurled circumferential surface or a button comprising on its outer circumferential surface at least one groove that extends or at least 10 grooves that extend in a plane or in planes comprising a longitudinal axis of the mechanical module. There may be less than 100 grooves. The electronic module may comprise an adapter element that may comprise an inner circumferential surface that is shaped inverse to the outer surface of the button, e.g., having protrusions corresponding to the grooves. The adapter element may be configured to form fit and/or to force fit to the button. The adapter element may be a separate part, e.g., molding may be simpler, from a casing of the electronic module. Alternatively, the adapter element may be part of the casing of the electronic module, e.g., there are less parts, logistic is simple, etc. Form fit and force fit are simple connection means. However, other removable connections may also be used, for instance screwing, e.g., screwing the electrical module to the mechanical module using an inner screw thread on the electronic module and an outer screw thread on the mechanical module or vice versa.

The electronic module may comprise a chassis. The chassis may comprise an annular wall that may form a compartment for the electronic unit. The chassis may carry the electronic unit. The chassis may be housed by a housing part of the electronic unit. The chassis may be a separate component or element from the housing part and may be assembled with the housing part as described below. Alternatively, the chassis may be integral to the housing part, e.g., formed as one molded part. The usage of a separate chassis may make assembling of the electronic module easier compared to assembling without usage of a separate chassis. The chassis may be made of a plastic material, preferably produced by injection molding. The material may be transparent for the radiation of the applied wavelength in order to allow transmission of optical radiation that is used by the detection unit, for instance for infrared radiation. However, there may be two different materials used for the chassis wherein the material that is used for the optical guide is more transmissive for the relevant wavelength of optical or electromagnetic radiation than the other material.

At least one adapter element may be used that is connected to the housing part, preferably by at least one snap fit connection. The adapter element may be used to adapt the electronic module to the mechanical module, for instance as mentioned above, e.g., knurled surface and/or grooves. Alternatively the adapter element may be formed integrally with the housing part. A lid may be used that is configured to be released from the chassis and/or from the housing part. The lid and/or the adapter part may be removable from the electronic module, for instance in order to change a battery and/or an accumulator.

A further aspect of the disclosure relates to a mechanical module, preferably the mechanical module of the modular system according to any one of the previous mentioned embodiments, comprising:

- a distal end and a proximal end, and
- a mechanism that is configured to set and/or to deliver a dose of the drug out of the distal end of the mechanical module, wherein the mechanical module is configured to be removably mechanically coupled to an electrical module in a proximal end region of the mechanical module.

Thus, the features, advantages and technical effects that are valid for the modular system and its embodiments may also be valid for the mechanical module.

A next aspect of the disclosure relates to an electronic module, preferably the electronic module of the modular system according to any one of the previous mentioned embodiments, comprising:

- a detector unit, and
- an electronic unit that is operatively coupled to the detector unit, wherein the electronic module is configured to be removably mechanically coupled to a mechanical module in a proximal end region of the mechanical module.

Thus, the features, advantages and technical effects that are valid for the modular system and its embodiments may also be valid for the electronic module.

An aspect of the disclosure relates to using an electronic module, preferably using the electronic module according to any one of the embodiment or of the embodiments mentioned above, in a first modular system together with a first mechanical module for drug delivery, preferably the mechanical module according to any one of the embodiment(s) mentioned above, and thereafter in a second modular system together with a second mechanical module that is of the same type as the first mechanical module.

The electronic module may be connected to the second mechanical module after the first mechanical module has reached its end of life, e.g., the first mechanical module has made all mechanical drug delivery operations for which it was designed. A signal that indicates the end of life of the first mechanical module may be generated by the electronic module that may record or trace the number of drug delivery operations and that may compare the traced number to a maximal number that may be stored in a memory of the electronic module. The electronic module may be used for more than two, three, four or for more than four mechanical modules or drug delivery devices. The number of drug delivery devices for which the electronic module may be used may be less than or equal to 1000 or 10000, especially if used together with single dose/use autoinjectors.

The extension feature and/or the light guide may be formed integrally with a chassis part of the electronic module, preferably as one part comprising the same material and comprising a homogenous material density. There may be no border surfaces between the chassis and the extension feature and/or the light guide, preferably no border surfaces that have normal vectors directed to one another. Thus, only one single chassis/optical guide part has to be produced for each electronic module.

The keying/blocking feature may be a separate component from a casing of the electronic module and/or from a chassis of the electronic module. The keying/blocking feature may be fastened to the electronic module and/or to the chassis of the electronic module. The keying and/or blocking feature may comprise at least one water-tight seal element. Water or humidity may be prevented to ingress the PCB (Printed Circuit Board) or PCB assembly (PCBA). Press fit, form fit, snug fit, force fit or other connection means may be used to connect the keying and/or blocking feature to the casing and/or to the chassis.

The chassis of the electronic module may comprise at least one wall element between the light pipe and the compartment for the electronic unit that is mentioned above. The wall may block a potting material or a potting compound from the extension feature, e.g., form the optical guide. There may be a gap between a bottom of the wall and a substrate, e.g., a PCB (Printed Circuit Board), of the electronic unit that may be arranged within the compartment. The gap may be filled with potting material or a potting compound and may secure the chassis and the PCB or substrate to each other.

Some of the electronic elements of the electronic unit may be only partially surrounded by the potting compound. Complete coverage may not be necessary for electronic components that comprise their own housing or package. Less molding compound may be used. Hardening of the molding compound/material may be faster, etc.

The indicator element may be part of a clutch element of the mechanical module, e.g., drug delivery device. There may be drug delivery devices in which such a clutch element is the most proximal moving element that is especially appropriate for the detection of the size of the dose that is selected and/or delivered.

A next aspect relates to a method of using a modular system for a drug delivery device, preferably using the modular system according to any one of the preceding embodiments or claims, comprising:

- assembling a first mechanical module and an electronic module thereby providing a first modular system, wherein the first mechanical module comprises a drug,
- using the first modular system for drug delivery, separating the first mechanical module and the electronic module after drug delivery, e.g., disassembly, assembling the electronic module and a second mechanical module that is of the same type as the first mechanical module thereby providing a second modular system, using the second modular system for drug delivery of a drug that is comprised in the second mechanical module.

Preferably, the electronic module may be mechanically coupled or may be coupleable to the mechanical module in a proximal end region of the mechanical module. The mechanical module and the electronic module may be removably coupled/connected to each other or may be coupleable/connectable to each other.

The electronic module may be an electronic module according to a further aspect of the disclosure which was manufactured using special filling methods as described below. Thus, the same technical effects as mentioned below apply to the electronic module, for instance excellent protection of electro-mechanical or opto-electronic parts/components as well as of electronic parts/components.

The first mechanical module may be structurally and/or functionally identical or similar to second mechanical module. Thus, the features, advantages and technical effects that are valid for the modular system and its embodiments may also be valid for the method of using the modular system.

Furthermore, an electronic module for a drug delivery device is provided, preferably an electronic module according to the embodiment mentioned above, comprising:

a circuit carrier which comprises at least one component surface, a first electrically operable component of a circuitry arranged on the at least one component surface, a module part comprising at least one side wall, wherein the side wall is arranged adjacent to the circuit carrier, wherein the side wall and the circuit carrier cooperate to delimit a receiving space for a filling layer, and wherein the filling layer contacts at least one, at least two or all of the side wall, the first electrically operable component or the component surface.

The proposed electronic module for a drug delivery device may comprise:

a circuit carrier which comprises at least one component surface, a first electrically operable component of a circuitry arranged on the at least one component surface, a module part comprising at least one side wall, wherein the side wall is arranged adjacent to the circuit carrier, wherein the side wall and the circuit carrier cooperate to delimit a receiving space for a filling layer, and wherein the filling layer contacts at least one, at least two or all of the side wall, the first electrically operable component or the component surface, e.g., at least one area/region of the component surface.

The filling layer may extend from the side wall to the first electrically operable component and/or from the side wall to the circuit carrier. The filling layer may preferably extend continuously and/or uninterrupted from the side wall to the first electrically operable component and/or from the side wall to the circuit carrier. Thus, the filling layer may provide an excellent protection for the first electrically operable component and/or for further electrically operable components carried by the circuit carrier.

The filling layer may be a non-conformal layer which does not maintain the topography of an underlying or adjacent surface. The thickness of the filling layer may be greater than the thickness of a conformal layer which preserves topography. The filling layer may prevent access to electrically operable components and/or may provide protection against environmental ingress, e.g., dust, humidity, etc.

A mechanically contacting surface of the filling layer may conform to the contour of the circuit carrier and/or of the first electrically operable component. The filling layer may be an electrically insulating layer. There may be the following conforming features:

a side surface of the filling layer may have the same contour as a surface of the sidewall which is contacted, for instance both arc-shaped, and/or a side surface of the filling layer may have the same contour as a side surface of the electrically operable component, for instance around the whole or at least part of the circumference of the electrically operable component, for instance at an rectangular edge there may be a concave edge in the filling layer and a convex edge on the electrically operable component, and/or a surface region (area) of the filling layer which is adjacent to the circuit carrier may have the same shape/form as the component surface of the circuit carrier, for instance both may be plane surface regions.

The module part may be a mechanical module part, e.g., a module part without electrically conductive components. The module part may be an outer housing part or an inner housing part (module chassis). The module part may also be a carrier, for instance, the module part may carry mechanical connection elements and/or light pipes etc., see for instance description of the Figures mentioned below.

The module part and the circuit carrier may be two parts which are manufactured separately from each other. The module part and the circuit carrier may comprise different materials if compared with each other. Both parts may be assembled in an assembling process. The filling layer may fasten both parts to each other. Thus, the filling material may adhere to the circuit carrier and/or to the module part and/or to the first electrically operable component.

The side wall of the module part may comprise a side wall which is oblique to the circuit carrier and/or a sidewall which faces radially inwards. Thus, both parts may form a well which is appropriate to be filled at least partially by a liquid filling material which forms the solid filling layer after curing. The circuit carrier may form a bottom of the well. The well may comprise a bottom (circuit carrier) and the side wall of the module part if the circuit carrier is arranged such that the component side faces upwards. The usage of the filling layer may allow to use the electronic module several times on several drug delivery devices. Thus, environmental impact and costs of electronic parts in the electronic module may be reduced considerably.

"Electrically operable" may involve using electrical current and/or electrical voltage for operation. The electrically operable component may be an active electronic element, e.g., a transistor, or a passive electronic element (e.g., capacitor, resistor, inductor), or a switch, for instance micro-switch which is also electrically operable, for instance electro-mechanical operable, e.g., it is possible to detect the state of the switch (on or off) using electrical current and/or electrical voltage.

The relation between the bounding element and the circuit carrier may be rotationally fixed and/or fixed against axial translational movement by the filling layer and/or by additional mechanical supporting parts.

The circuit carrier may comprise a plurality of conductive paths of an electrical circuitry on a surface of the circuit carrier pointing away from the component side and/or on a surface adjacent to the component side. Alternatively or additionally, the conductive paths may be arranged between two main surfaces of the circuit carrier. Main surfaces may be the surfaces with the largest surface area compared for instance to side surfaces of the circuit carrier. The main surfaces may be arranged parallel to each other or essentially parallel to each other. A flexible or a rigid circuit carrier may be used.

The circuit carrier may comprise or may consist of FR4 (Fire Resistant), e.g., glass fiber and epoxy resin material. A single layer or a multi-layer circuit board may be used. The circuit board may be named as printed circuit board. Electrically conductive tracks, pads and other features may be etched from one or more sheet layers of metal, for instance copper, laminated onto and/or between non-conductive substrate layers. This may look like printed. Alternatively, printing technologies may be used to produce the printed circuit board. The circuit carrier was named as substrate in the first part of the description.

SMD (Surface Mounting Devices) may be used to solder the electronic components to the circuit board. Alternatively, other connection techniques may be used.

The side wall may be circumferentially closed and/or may be adjacent to the filling layer, e.g., along the whole circumference of the side wall or along at least half of the circumference. The circumference may be an inner circumference.

The electronic module may comprise a second electrically operable component of the circuitry, and/or at least one further electrically operable component of the circuitry. The following features may be realized:

- wherein the first component has a first construction height measured from the component surface,
- wherein the second component has a second construction height measured from the component surface,
- wherein the second construction height is greater than the first construction height,
- wherein the first electrically operable component is embedded into the filling layer at most to the first construction height, and
- wherein the second electrically operable component is embedded into the filling layer at least up to the second construction height or up to a third height which is greater than the first construction height but less than the second construction height.

The component surface may be a plane surface. The different construction heights may result in a specific topography or three-dimensional profile of the top surfaces of the components. This topography may be different from a plane. Therefore, it may not be possible to use conventional casting or potting techniques in order to produce the filling layer. It may be for instance necessary to prevent that the filling layer reaches mechanically movable parts and/or optical parts which have lower construction heights than other components which have to be covered by or embedded into the filling layer up to a height which is above the height of the mechanically movable parts.

The second height and/or the third height may be higher than the first height by at least 10 percent, at least 20 percent, at least 30 percent, at least 50 percent, at least 75 percent or at least 100 percent of the first height. However, the second height may be lower than 1000 percent of the first height to give only one example.

Thus, the first component (shallower component) may not be covered by the filling material of the filling layer. The second component (taller component) may be covered by the filling material of the filling layer.

The construction height may be identical or corresponding to a height given in a catalog if the component is mounted with no distance to the component surface of the circuit carrier. There may be deviations to a height given in a catalog if there is a space between a lower surface of the component and the component surface, for instance if longer contact wires are used, e.g., in order to ease assembly.

The filling layer may comprise a first profile in a first cross section which is perpendicular to the component surface. In the first cross section, the thickness of the filling layer may be lower in the two peripheral regions compared to a central region. The first electrically operable component may be arranged in one of the peripheral regions. The filling layer may comprise a second profile in a second cross section which is perpendicular to the component surface and perpendicular to the first cross section. In the second cross section, the thickness of the filling layer may be lower in the two peripheral regions compared to a central region. The second electrically operable component may be arranged in a central region. The first profile of the filling layer may be a result of the usage of a high viscosity filling material and/or of a filling material which is hardened or cured before it flows from a central region to the peripheral region. Thus, an easy to realize potting method is provided which enables a lower fill height in peripheral regions compared, for instance, to the central region or to another peripheral region where the filling material is filled in first. The shape of the free surface of the filling layer, e.g., the surface which faces away from the component surface, may be the result of using a highly viscous filling layer and/or of curing the filling layer before it reaches the first height on the first component. In an embodiment, each peripheral region of the filling layer may have lower height of filling layer compared to a central region or to the central region.

Alternatively, the filling layer may comprise a first profile in a first cross section which is perpendicular to the component surface. In the first cross section, the thickness of the filling layer may increase from a first thickness in a first one of the peripheral regions to a second thickness in a central region to a third thickness in a second one of the peripheral regions. The first electrically operable component may be arranged in the first one of the peripheral regions, e.g., in a region with low fill height or thickness of the filling layer. Preferably, the filling layer may comprise a second profile in a second cross section which is perpendicular to the component surface and perpendicular to the first cross section. In the second cross section, the thickness of the filling layer may be constant or may deviate only by at most two percent or by at most five percent from a maximum filling height/thickness of the filling layer, e.g., measured from the component surface.

Thus, the filling layer may comprise a surface which faces away from the component surface. An inclination angle between the surface of the filling layer which faces away from the component surface and the component surface may be at least 5 degrees, at least 10 degrees or at least 15 degrees. The inclination angle may be less than 40 degrees to give only one example. The inclination angle and/or the first profile may be the result of casting the filling material onto the circuit carrier using an inclination angle of the circuit carrier with regard to a horizontal plane. This may be a simple measure in order to have different thicknesses of the filling layer and to make sure that comparably shallow components are not covered by the filling layer, for instance components with mechanically movable parts.

The inclined surface may be essentially plane and/or may extend lateral via at least two electrically operable components and/or extend lateral via a plane surface of the second electrically operable component which may be parallel or essentially (within manufacturing tolerances) parallel to the circuit carrier or to the component surface.

In alternative embodiments, the electronic module may again comprise a second electrically operable component of the circuitry. The first electrically operable component may again have a first construction height measured from the component surface. The second electrically operable component may again have a second construction height measured from the component surface. The second construction height may be greater than the first construction height. The first electrically operable component and/or the second electrically operable component may be embedded into the filling layer at most to the first construction height. The second electrically operable component may be sealed by a combination of the filling layer and at least one further sealing element being different from the filling layer, preferably different with regard to material of filling layer and/or thickness of filling layer and/or being another component compared to the filling layer, e.g., another type of protection feature. The combination of two sealing features may allow the realization of advanced sealing techniques which allow small thicknesses of the filling layer.

The second height may be higher than first height by at least 10, 20, 30, 50, 75 or 100 percent of the first height. The second height may be higher than first height by at most 1000 percent to give only one example. The construction height may be identical or corresponding to a construction height given in a catalog for the electrically operable components if the components are mounted with no distance to the component surface. There may be a deviation to a construction height given in a catalog if there is a space between a lower surface of the component and the component surface, for instance because of use of longer contact wires.

The further sealing element may be a coating layer. The second electrically operable component may comprise the coating layer on the surface which is farthest away from the circuit carrier and at least partially also on its side surfaces. The coating layer may extend to the filling layer and/or may be in contact with the filling layer. The top surface of a component may be the surface which is opposite to base surface which directs to the surface of the circuit carrier or which is adjacent to surface carrier. The coating layer may not cover a bottom surface of the second component.

Optionally, the coating layer may extend to the component surface and/or may be in contact with the component surface. This may be the case, if the coating layer is applied to the second electrically operable component in a state where the second electrically operable component is already mounted on the circuit carrier, e.g., on the component surface.

The coating layer may be applied before the second electrically operable component is mounted or after mounting of the second electrically operable component to the circuit carrier. The coating layer may cover the sidewalls of the component only partially, e.g., not completely, or completely. If the coating layer is applied after the second component is mounted on the circuit carrier, it is possible to protect prominent features of the second component by the coating layer and to protect regions near to the component surface by the filling layer, especially regions within slots or narrow spaces between adjacent components.

A conformal coating method may be used for producing the coating layer. Conformal may mean that the topography (three-dimensional profile) of the surface is preserved in the coating layer, for instance edges (elongated edges) and corners. The usage of a coating layer in combination with the filling layer may enable advanced sealing or protection schemes and/or allow to reduce the amount of filling material for producing the filling layer. Furthermore, the usage of an additional coating layer may allow to use a filling layer having a small thickness, for instance in order to not to cover shallow components comprising mechanical and/or optical elements, and to also seal at least one component having a comparably large construction height.

The coating layer may comprise or consists of a coating material, preferably of only one coating material in order to enable simple manufacturing. The coating material may comprise or consists of silicone. Silicone is water resistant and/or damps mechanical impact. A spray may be used to produce the coating layer, for instance MasterBond®, e.g., UV (ultra violet curable) 10-MED which may be appropriate for application in medical devices and/or drug delivery devices.

Alternatively, the further sealing element may be an integral cover for the second electrically operable component which is integral with the module part. The second component may be sealed by the integral cover and by the filling layer into which the integral cover is embedded at least partially and/or fully.

An integral cover may nevertheless allow easy assembling, if the module part is arranged only on one side of the circuit carrier and/or if the circuit carrier is inserted into the boundary element from a side which is opposite to the side which comprises the integral cover.

In other embodiments, the cover of the second component is not integral to the module part but is held before applying the filling material by other measures around the second component. After the application of the filling material, the cover may be held or fixed by the filling material. In all cases, there may be on at least one side or on all sides a lateral and/or an axial space between the cover and the second component.

The combination of the cover and of the filling layer may allow easy sealing of components having significant differences in construction height.

The integral cover may comprise at least one flat surface. The flat surface may comprise a marking and/or carry a label, for instance a paper label and/or a plastic label or a plastic-coated label. The flat surface may be arranged in parallel to a main surface of the circuit carrier, e.g., in parallel to the component surface. The marking may be a laser marking, e.g., a marking which was melted into the material of the cover using a laser. The marking may be printed, e.g., a marking applied by means of a pad printing process. The surface which carries the marking and/or the label may be an outer surface of the cover. The marking may identify the type of the module and/or or quality class and/or a serial number.

In the embodiments which use a further sealing element being different from the filling layer, the filling material may form a free plane surface which may be parallel or essentially parallel to the circuit carrier. Thus, it may not be necessary to tilt the module during casting of the filling material of the filling layer and/or to use fast curing.

Essentially parallel, may refer to an inclination angle between the free surface and the component surface in the range of zero to 3 degrees or of zero to 1.5 degrees.

The free and/or plane surface may point away from the circuit carrier. This free surface may be different from the lower border surface of the filling material which forms the border between the circuit carrier and the filling material and which is adjacent to the component surface of the circuit carrier.

The module part may comprise or carry at least one optical guiding structure which may be configured to guide light generated by at least one light emitting component on the circuit carrier. Thus, light guides or light pipes may be used to implement a sensor which detects the dose set by a user and/or the dose injected by a drug delivery device onto which the electronic module is mounted or of which the electronic module is part of. There may be only a narrow hole or slit which allows the detection of the movement of movable parts of a drug delivery device comprising tightly packed parts.

The first component may be an electro-mechanical component comprising at least one movable part which is movable with regard to a housing of the electro-mechanical component or to another part of the electro-mechanical component. The first component may be or may comprise for instance switch, a mechanical switch, a micro-switch, etc. Alternatively, the first electrically operable component may be an electro-optical component. The electro-optical component may be or may comprise a light emitting diode (LED), an infrared diode (IR), a photosensor, etc.

The second electrically operable component or may be an electronic component, e.g., a component without movable and/or optical parts. Thus, the second component may be preferably a purely electronic component, e.g., resistor, capacitor, inductor, transistor, integrated circuit. Alternatively, the second component may be or may comprise and integrated circuit, for instance a Bluetooth® or a ZigBee® transmitter and/or receiver and/or a sending unit according to another transmitting protocol.

The first component may be arranged at the periphery or more to periphery of circuit carrier compared to the location of the second component. The second component may be arranged more central if compared to the location of the first component. Thus, the filling material may be poured or dropped centrally, preferably for the variant which uses viscous filling material or for the variant with inclination during filling. Both variants are mentioned above. The technical effect may be that for instance a movable component of the first component is not blocked by filling material. Nevertheless, an appropriate sealing of other components may be provided by the filling layer.

The electronic module may comprise at least one, at least two or all three of the following:

- an electrical power source, which is carried by the module part or by a mechanical carrier, and/or
- a delivery button which comprises a delivery surface which is configured to be pressed in order to initiate the delivery of a drug from a drug delivery device, which is carried by the module part or by the mechanical carrier, and/or wherein the delivery surface is preferably arranged essentially parallel or is arranged parallel to the circuit carrier, and/or

- a lateral setting surface which is configured to be used to set a dose of the drug (Dr) for delivery, wherein preferably the setting surface faces radially from an axis of the electronic module.

The delivery surface may be an axially (proximally) facing surface. A main axis of the electronic module may be arranged on the linear extension of a longitudinal axis of a drug delivery device if the electronic module is arranged on the drug delivery device. Therefore, the main axis of the electronic module may be named as a longitudinal axis too. However, the longitudinal length of electronic module may be comparably short compared for instance to its diameter, e.g., shorter.

The power source may comprise or be a battery (not rechargeable) or an accumulator (rechargeable). The delivery surface may be for instance arranged parallel to the circuit carrier and/or parallel to a main surface of the battery/accumulator. Thus, the components of the electronic module may be packed tightly with only small distances between adjacent components. The overall assembly space may be kept small in this way.

The setting surface may be for instance inclined with regard to delivery surface, for instance with an angle in the range of 80 degrees to 100 degrees. Thus, setting of a dose of a medicament or drug may be possible by rotation of the setting surface, e.g., around the main axis of the electronic module which may correspond to the main axis of a drug delivery device which comprises the electronic module or onto which the electronic module is mounted.

A further aspect of the disclosure relates to a method of manufacturing an electronic module for a drug delivery device, comprising:

- providing a circuit carrier which comprises at least one component surface, wherein the circuit carrier carries a first electrically operable component of a circuitry on the at least one component surface,

- providing a module part comprising at least one side wall,
- forming a well by arranging the side wall adjacent to the circuit carrier, and
- casting or pouring or filling a filling material of a filling layer into the well between the first component and the side wall.

A liquid or viscous filling material may be used in order to form the filling layer. The electronic module may be assembled after providing the filling layer or before providing the filling layer.

The module part may be a casing/housing or a chassis, e.g., an inner casing, inner supporting structure or inner housing which is surrounded by an outer housing of the electronic module.

The same technical effects mentioned above for the electronic module may also apply to the method if the corresponding features are realized.

The circuit carrier may also carry the second electrically operable component of the circuitry.

The method may further comprise:

- ensuring (a) that the first electrically operable component is embedded into the filling layer at most to the first construction height and that the second electrically operable component is embedded into the filling layer up to at least the second construction height or up to at least a third height which is more than the first construction height but preferably less than the second construction height, or ensuring (b) that the second electrically operable component is sealed by a combination of the filling layer and at least one further sealing element different from the filling layer.

The method may be used to produce an electronic module according to one of the embodiments mentioned above.

The method may comprise at least one, at least two, at least three of all four of the following:

(a1) using a highly viscous filling layer and/or using energy radiation curing in order to ensure that the filling layer sets and/or hardens before rising to the level of the first component, (a2) inclining the well and/or the module and/or the circuit carrier during casting of the filling layer, (b1) using a coating layer on the second electrically operable component, (b2) using an integral cover on the module part in order to seal the second electrically operable component.

A combination of for instance a1) and a2) may be used. Other combinations of variants a1, a2, b1 and/or b2 are possible as well.

The making and using of the presently preferred embodiments are discussed in detail below. It should be appreciated, however, that the present disclosure provides many applicable concepts that can be embodied in a wide variety of specific contexts. The specific embodiments discussed are merely illustrative of specific ways to make and use the disclosed concepts, and do not limit the scope of the claims.

Moreover, same reference numerals refer to same technical features if not stated otherwise. As far as "may" is used in this application it means the possibility of doing so as well as the actual technical implementation. The present concepts of the present disclosure will be described with respect to preferred embodiments below in a more specific context namely drug delivery devices, especially drug delivery devices for humans or animals. The disclosed concepts may also be applied, however, to other situations and/or arrangements as well.

The foregoing has outlined rather broadly the features and technical advantages of embodiments of the present disclosure. Additional features and advantages of embodiments of the present disclosure will be described hereinafter, e.g., of the subject-matter of dependent claims. It should be appreciated by those skilled in the art that the conception and specific embodiments disclosed may be readily utilized as a basis for modifying or designing other structures or processes for realizing concepts which have the same or similar purposes as the concepts specifically discussed herein. It should also be recognized by those skilled in the art that equivalent constructions do not depart from the spirit and scope of the disclosure, such as defined in the appended claims.

BRIEF DESCRIPTION OF THE FIGURES

For a more complete understanding of the presently disclosed concepts and the advantages thereof, reference is now made to the following description in conjunction with the accompanying drawings. The drawings are not drawn to scale. In the drawings the following is shown in:

FIG. 3 a modular system of a third embodiment,

FIG. 4 a modular system of a fourth embodiment,

FIG. 5 an electronic circuit,

DETAILED DESCRIPTION

Figures 1, 2:
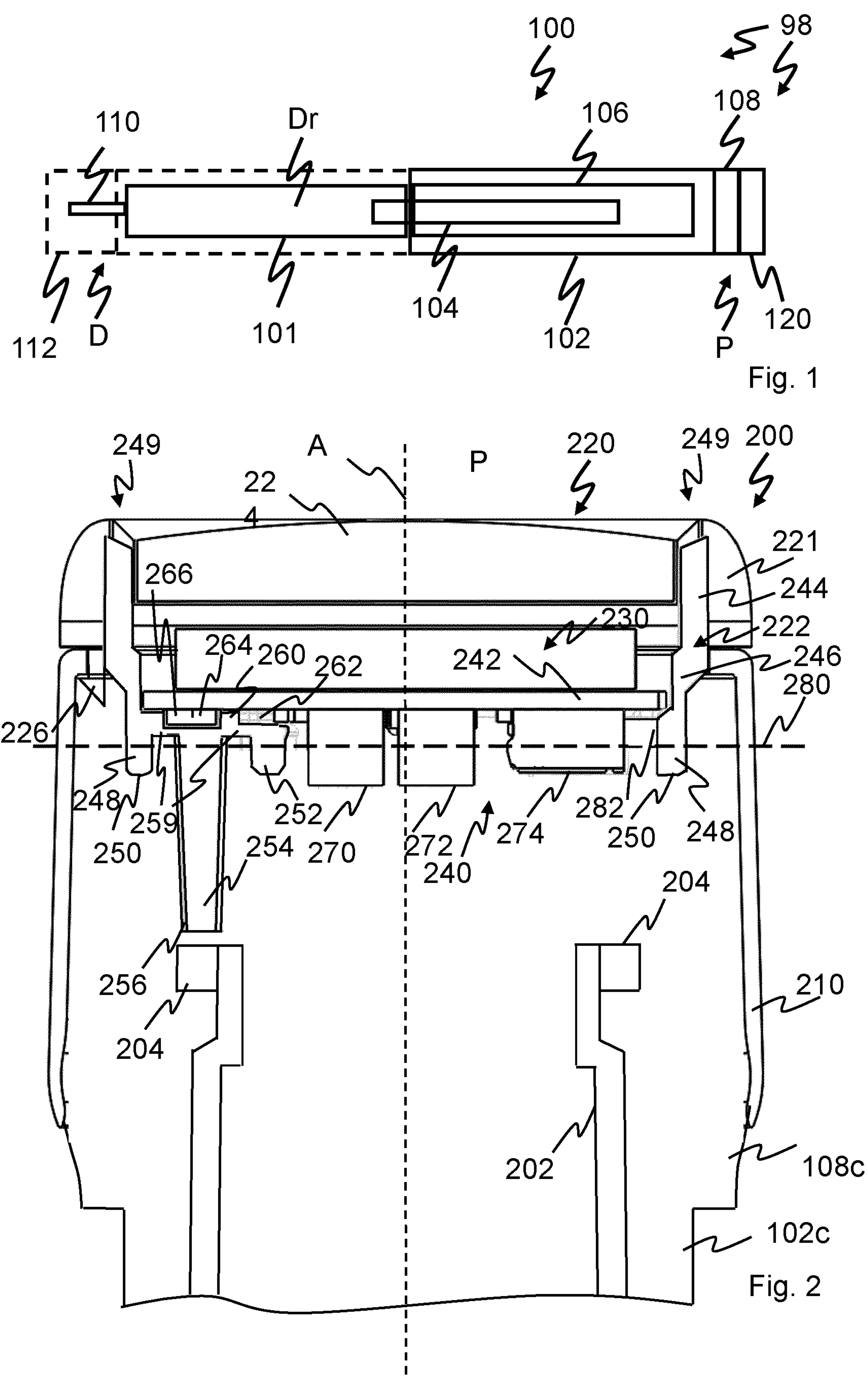
FIG. 1 a modular system according to a first embodiment.
FIG. 2 a modular system of a second embodiment.

FIG. 1 illustrates a modular system 98 according to a first embodiment. Modular system 98 may comprise a drug delivery device 100 that may comprise a container retaining member 101 and a main housing part 102. Container retaining member 101 may comprise a drug Dr. Main housing part 102 may house or surround the container retaining member 101 completely or partially and may comprise further parts of the drug delivery device 100. Alternatively, the main housing part 102 may be connected to the container retaining member 101 but may not surround it and even may not surround a part of the container retaining member 101, see dashed line in FIG. 1.

Within the main housing part 102 the following components may be arranged:

- a piston rod 104 that is adapted to move the piston that may be arranged within container retaining member 101,
- a driving mechanism 106 for the piston rod 104. The driving mechanism 106 may comprise an energy storing element, for instance a spring that is loaded manually before each use. Alternatively, the energy storing element may be loaded for instance during assembling of drug delivery device 100. Alternatively, a manually driven driving mechanism may be used, e.g., without an energy storing element that is used to drive piston rod 104.
- for instance, at a proximal end P, an actuating element 108 that is used for the initiation of a movement of piston rod 104 into the container retaining member 101, whereby the driving mechanism 106 is used. Alternatively, an autoinjector device may be used that is actuated by an axial movement of a movable needle shroud (not shown). An actuating element or a dosing element may be used to dial the size or amount of a dose of drug Dr in some embodiments.
- a cap 112 that may be attached to main housing part 102 or to another part of drug delivery device 100. Cap 112 may be an outer cap that may include a smaller inner cap which protects a needle 110 directly.

If drug delivery device 100 is not an autoinjector, a dial sleeve may be screwed out of main housing 102 and may be pressed by a user in order to move plunger rod 104 distally and to inject drug Dr.

Drug delivery device 100 may be a single use or a multiple use device.

Drug Dr may be dispensed from the container through needle 110 or through a nozzle that is connectable and/or connected to the distal end D of drug delivery device 100. Needle 110 may be changed before each use or may be used several times.

Modular system 98 may comprise an electronic module 120 that is mechanically connected to a proximal end region P of drug delivery device 100, for instance to a proximal end region P of actuating element 108. Modular system 98 is described below in more detail, see FIG. 2 and corresponding description.

Electronic module 120 may be used not only for drug delivery device 100 but also for other drug delivery devices that are similar or identical to drug delivery device 100. Thus, electronic module 120 is used multiple times with different drug delivery devices in different modular systems 98, etc. Furthermore, the diameter of drug delivery device 100 is not increased by electronic module 120 promoting excellent handling of modular system 98, and especially of drug delivery device 100.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

FIG. 2 illustrates a modular system 200 of a second embodiment that may be the same as the first embodiment. However, more details are shown in FIG. 2. Modular system 200 may comprise for instance a housing part 102*c* that may correspond to housing part 102 described above. An actuating element 108*c* may correspond to actuating element 108 described above.

Proximal part P of modular system 200 may comprise:

- a clutch element 202 or other rotatable or moving element that may comprise radially protruding features 204, for instance teeth of a sprocket or of a sprocket sleeve,
- an essentially annular adapter element 210 that may encompass the side wall of actuating element 108,
- an electronic module 220 that may correspond to electronic module 120 and that may comprise an electronic unit 240. Electronic unit 240 is described below in more detail.
- an annular casing or housing 221 of electronic module 220,
- a chassis 222 within electronic module 220. Chassis 222 may comprise an annular wall 249 surrounding a compartment for electronic unit 240 and/or for several other parts.
- and a lid 224 of electronic module 220.

Hooks may be used to connect housing 221 and adapter element 210, see for instance hook 226, e.g., a snap fit connection. Alternatively, other connection means may be used or housing 221 and adapter element 210 may be formed integrally as one single part.

The following electronic components may be comprised within electronic module 220:

- a battery 230 or a rechargeable accumulator, and
- an electronic unit 240 that may form a PCBA (Printed Circuit Board Assembly).

Electronic unit 240 may comprise:

- a printed circuit board 242 (PCB) which may be named as substrate in the claims,
- at least one light source 264, e.g., an IR (Infra-Red) light source, or two light sources,
- at least one optical sensor 266 or at least two optical sensors,
- a transmitter unit 270, for instance a transmitter unit 270 that operates according to the Bluetooth® protocol, for instance for communication with a smartphone or other computer device,
- a receiver unit 272, for instance a receiver unit 272 that operates according to the Bluetooth® protocol, for instance for communication with a smartphone or other computer device, and
- an optional switch 274, for instance a micro switch.

FIG. 2 shows a longitudinal axis A of modular system 200. Electronic module 220 may be arranged proximally of actuating element 108*c* of the corresponding drug delivery device. Electronic module 220 and actuating element 108*c* are arranged symmetrically to axis A whereby electronic module 220 and actuating element 108*c* are in physical contact with each other, mainly via adapter element 210. Adapter element 210 may be plugged mechanically onto actuating element 108*c*.

Chassis 222 may comprise:

- three annular wall portions 244, 246 and 248 of an annular wall 249,
- a distal end 250 of chassis 222 and at the same time of annular wall portion 248,
- a wall 252 of chassis 222, and
- at least one optical guide 254 or at least two optical guides which may have the same shape and or coating as optical guide 254.

Optical guide 254 may be coated with a coating 256, see for instance first part of the description, e.g., metal coating and/or carbon fiber coating and/or soft coating.

A cup like structure may be formed by wall 252 and by a part of annular wall portion 248 around a proximal part or base part of optical guide 254. The cup like structure may comprise a laterally extending thinner portion 259 that may be regarded as a bottom portion of the cup like structure. Thinner portion 259 may be arranged near to but distally of a light source 264, e.g., IR, and of an optical sensor 266. A rib 260 may be arranged on thinner portion 259 and may extend proximally P up to printed circuit board 242. Rib 260 may be adjacent to light source 264, e.g., IR, and/or optical sensor 266. There may be a gap 262 between printed circuit board 242 and thinner portion 259 and/or a proximal or bottom portion of wall 252. Gap 262 may be filled with a potting compound/material 282. Rib 260 may protect light source 264, e.g., IR, and/or optical sensor 266 against potting compound/material 282 if it is in its melted state. The contact surface between potting compound/material 282 and chassis 222 may be increased by gap 262 thus promoting a mechanical connection between chassis 222 and potting compound 282 or potting material.

There may be a sequence of annular wall portion 244, 246 and 248 in this order from proximal P end to distal end of annular wall 249. Annular wall portion 244 may have a first diameter that corresponds to the diameter of lid 224. Annular wall portion 246 may have a second diameter that is less than the first diameter. The second diameter may correspond to the diameter of printed circuit board 242 (PCB). Furthermore, annular wall portion 248 may have a third diameter that is less than the second diameter.

A fill height 280 measured from PCB 242 may be in the range of 2 mm to 7 mm. The fill height 280 of the potting compound 282 or material may be selected appropriately, for instance to cover only a part of some of the electrical parts of electronic unit 240. The inner side of distal end 250 of annular wall portion 248 may not be covered by potting compound 282 or by another potting material. However, the more proximal regions of inner side of annular wall portion 248 may have contact to potting compound 282 or to another potting material. During potting printed surface board 242 is below potting compound 282 and annular wall portion 248 forms a lateral border for the melted or malleable potting compound. After hardening of potting compound 282, chassis 222 may be arranged again in all directions, for instance in the direction or position that is shown in FIG. 2. Potting compound 282 or potting material may be an electrical insulator. Wall 252 may protect the basis part of optical guide 254 against the potting compound/material 282 during potting.

Chassis 222 may comprise a keying/blocking feature similar to the keying/blocking features that are described in FIGS. 3 and 4. Alternatively, chassis 222 may not comprise such a keying/blocking feature.

FIG. 3 illustrates a modular system 300 of a third embodiment that may be similar to first modular system 98 or to second modular system 200. Modular system 300 may comprise:

- a chassis 222*a* of an electronic module. Chassis 222*a* may be similar or identical to chassis 222, see FIG. 2.
- a keying and/or blocking feature K1*a*, for instance an annular ring, that extends distally from chassis 222*a*.

There may be an inverse shaped keying feature K1*b* on an actuating/adjusting element 108*a* which may be similar or identical to actuating/adjusting element 108 or 108*c*. Furthermore, the drug delivery device that carries actuating/adjusting element 108*a* may be similar or identical to drug delivery device 100. Invers shaped keying feature K1*b* may be an annular groove having essentially the same or a slightly smaller inner diameter as annular ring K1*a* and the same outer or a slightly greater outer diameter as annular ring K1*a*.

An outer annular groove 310 for optical guides 254*a*, 258*a* may be separated by an annular ring 311 from annular groove of keying feature K1*b*. Optical guides 254*a*, 258*a* may extend into annular groove 310 if chassis 222*a* and/or the corresponding electronic module is mounted or assembled onto the drug delivery device that carries actuating/adjusting element 108*a*, e.g., onto actuating/adjusting element 108*a*. Optical guides 254*a*, 258*a* may extend the same length as keying/blocking feature K1*a* measured for instance from a circuit board within chassis 222*a*. Alternatively, optical guides 254*a*, 258*a* may be slightly shorter than keying/blocking feature. Alternatively, only one optical guide 254*a* or 258*a* may be used.

An optional central cylindrical portion 312 may be arranged at the longitudinal axis A of the drug delivery device that comprises actuating/adjusting element 108*a*. Central cylindrical portion 312 may prevent ingress of dust, wet and/or humidity into the drug delivery device.

Hooks 320 to 324 and/or rotation blocking elements may be used on chassis 222*a*. Hooks 320 to 324 and/or other rotation blocking elements may cooperate with grooves 330 at the outer circumferential surface of actuating/adjusting element 108*a*. Alternatively, an adapter element may be used that corresponds to adapter element 210, see FIG. 2. In the embodiment, three hooks 320 to 324 and/or rotation blocking elements are used that have same circumferential or angular distances to each other. However, more than three or less than three hooks 320 to 324 and/or rotation blocking elements may be used.

An optional further clip connection 326*a* and 326*b* or other connection element(s) may be used to connect chassis 222*a* to actuating/adjusting element 108*a*. Clip connection 326*a* may be opened by a user in order to release chassis 222*a* from actuating/adjusting element 108*a*.

In an alternative embodiment, keying feature K1*a* may be arranged on actuating/adjusting element 108*a*, see for instance annular ring 311, and chassis 222*a* may comprise a corresponding annular groove.

FIG. 4 illustrates a modular system 400 of a fourth embodiment. The following components may correspond to components of the modular system 300 of the third embodiment:

- a chassis 222*b* of electronic module may correspond to chassis 222*a*,
- an actuating/adjusting element 108*b* may correspond to actuating/adjusting element 108*a*,
- an optical guide(s) 254*b*, 258*b* may correspond to optical guide(s) 254*a*, 258*a*,
- an outer annular groove 410 may correspond to outer annular groove 310,
- a central cylindrical portion 412 may correspond to central cylindrical portion 312 except the modification that is mentioned below,
- optional hooks 420 to 424 and/or rotation blocking elements may correspond to hooks 320 to 324 and/or rotation blocking elements of chassis 222*a*, and
- optional further clip connection 426*a* and 426*b* may correspond to optional further clip connection 326*a* and 326*b*.

Chassis 222*b* may comprise a protruding keying feature K2*a* that may comprise two plate like elements that are arranged crosswise. An inverse shaped keying feature K2*b* on actuating/adjusting element 108*b* may comprise two corresponding slits 411*a*, 411*b* that allow insertion of keying/blocking feature K2*a* into inverse shaped keying/blocking feature K2*b*. The angle between slits 410 and 411 may have the value 90 degrees. However, other angles may also be used.

Keying/blocking feature K2*a* and inverse shaped keying/blocking K2*b* may fulfill an anti-rotation function for chassis 222. Therefore, hooks 420 to 424 and/or rotation blocking elements may be optional.

In an alternative embodiment, keying feature K2*a* may be arranged on actuating/adjusting element 108*b*, and chassis 222*b* may comprise corresponding slits.

Thus, chassis 222*a* only fits to drug delivery devices comprising keying and/or blocking feature K1*b*, i.e. an annular groove, but not to drug delivery devices comprising keying and/or blocking feature K2*b*, i.e. comprising two cross like slits 410, 411. In the same manner, chassis 222*b* only fits to drug delivery devices comprising keying and/or blocking feature K2*b*, but not to drug delivery devices comprising keying and/or blocking feature K2*a*.

FIG. 5 illustrates schematically an electronic unit 500, for instance electronic unit 240. Electronic unit 500 may comprise:

- at least one processor Pr or another control unit,
- a memory Mem, for instance volatile and/or nonvolatile storing memory,
- a battery Bat or a rechargeable accumulator or any other electrical power source,
- an output device Out, for instance a sending unit, for instance for communication with a smartphone or other computer device,
- an optional input device In, for instance for communication with a smartphone or other computer device,
- a switch Sw, and
- at least one sensor S or at least two sensors, preferably optical sensor(s).

Further parts may be comprised in electronic unit 500 that are not shown, for instance a radiation source, especially a light source.

Processor Pr may be a microcontroller or microprocessor that performs instructions of a program which is stored in memory M. Alternatively, an FPGA (Field Programmable Gate Array), ASIC (Application Specific Integrated Circuit), PLA (Programmable Logic Array), PLD (Programmable Logic Device) or another appropriate circuitry may be used to implement a finite state machine that does not perform instructions of a program.

Electronic unit 500 may implement a quadrature encoder, e.g., an encoder that uses amplitude modulation of two sensors having 180 degrees phase shift between two sensor signals, for instance anti phase sensor signals. Alternatively, other sensing methods may be used.

There may be two alternative modes of operation of sensing in accordance with various embodiments. According to a first alternative, a first sensor and a second sensor, for instance optical sensors, may be provided having an angular offset that is half of the periodicity of encoded regions of the encoder ring, for instance on clutch element 202. In the embodiment according to the first alternative, the sensors may be operated to sample synchronously, i.e. at the same times (t1; t2, t3, . . . ). This may ease signal detection and/or signal processing.

According to a second alternative, a first sensor and a second sensor, for instance optical sensors, may be provided having an angular offset that differs from half of the feature periodicity of encoded regions of the encoder ring. Therefore, sensors I and II may operate in a staggered mode with an offset in time (delta t) between samplings. This may be used to achieve more balanced overall system power consumption than available in synchronous operation.

One of the following sensing modes may be used:

1) static thresholding,
2) dynamic thresholding,
3) not using a threshold to detect low-high transitions of the sensor signals. However, a threshold for a voltage difference of the two sensor signals may be used. Furthermore, scaling factors for mean and amplitude may be used. The scaling factors may be set during manufacturing, for instance during a calibration method.
4) same as 3) but differing in that the scaling factors may be calculated after each dose delivery.
5) peak-detect method that does preferably not use the setting of thresholds to detect low-high transitions of the sensor signal(s) and that does preferably not use scaling of signals to match mean and amplitude.

FIGS. 6 to 9 refer to methods of manufacturing electronic modules 600, 700, 800 and 900, for instance of electronic modules 120, 300 mentioned above or of other electronic modules comprising components with different construction heights.

Electronic module 120, 220, 600, 700, 800 and 900 may comprise:

- a circuit carrier 242 (for instance a PCB) which comprises at least one component surface SF1,
- a first electrically operable component, for instance a switch 274, of a circuitry arranged on the at least one component surface SF1,
- a module part comprising at least one side wall 248, 248*a*, and a filling layer 620, 720, 820, 920, e.g., a potting compound 282, wherein the side wall 248, 248*a* is arranged adjacent to the circuit carrier 242, wherein the side wall 248, 248*a* and the circuit carrier cooperate to delimit a receiving space for the filling layer 282, 620, 720, 820, 920, and wherein the filling layer 282, 620, 720, 820, 920 contacts at least one, at least two or all of the side wall 248, 248*a*, the first electrically operable component or at least one area/region of the component surface SF1.

In the example according to FIG. 2, module part is a chassis 222 which carries printed circuit board 242 (circuit carrier), battery 230 and lid 224 which may be also named as a delivery lid comprising a delivery surface DSF. Grooves 330, 430 may be part of a setting surface SF0 which is used to set a dose.

Figure 6:
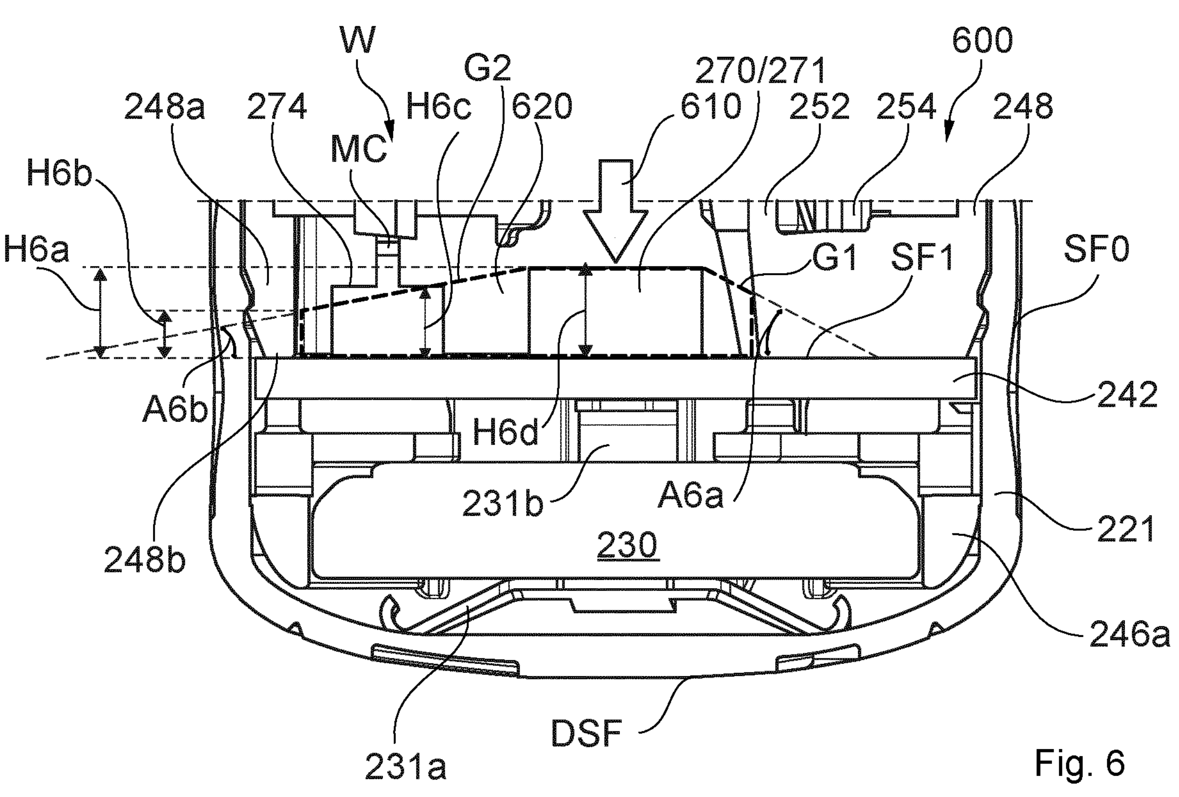
FIG. 6 a method step during the manufacturing of an electronic module of the modular system according to a first filling embodiment using highly viscous filling material, FIG. 7 a method step during the manufacturing of an electronic module of the modular system according to a second filling embodiment using conformal coating applied prior to filling, FIG. 8 a method step during the manufacturing of an electronic module of the modular system according to a third filling embodiment using an additional cover, preferably an integral cover to a chassis, and FIG. 9 a method step during the manufacturing of an electronic module of the modular system according to a fourth filling embodiment with inclination of the electronic module during filling.
Figure 7:
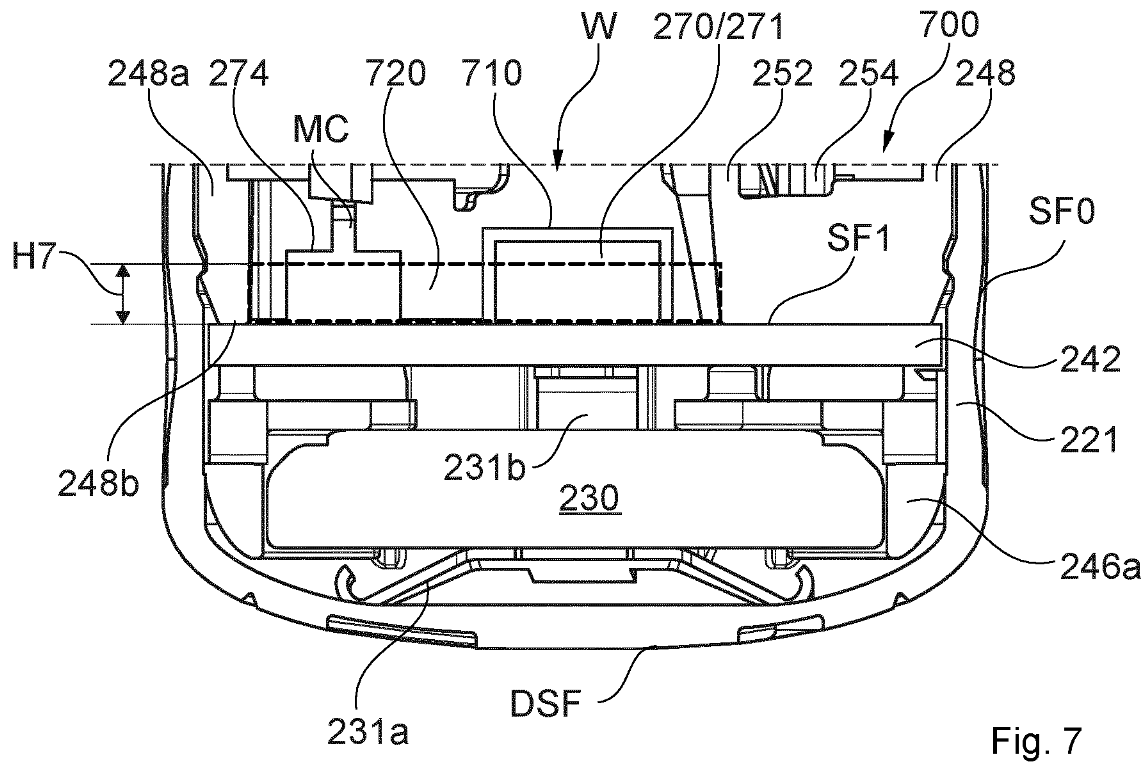
Figure 8:
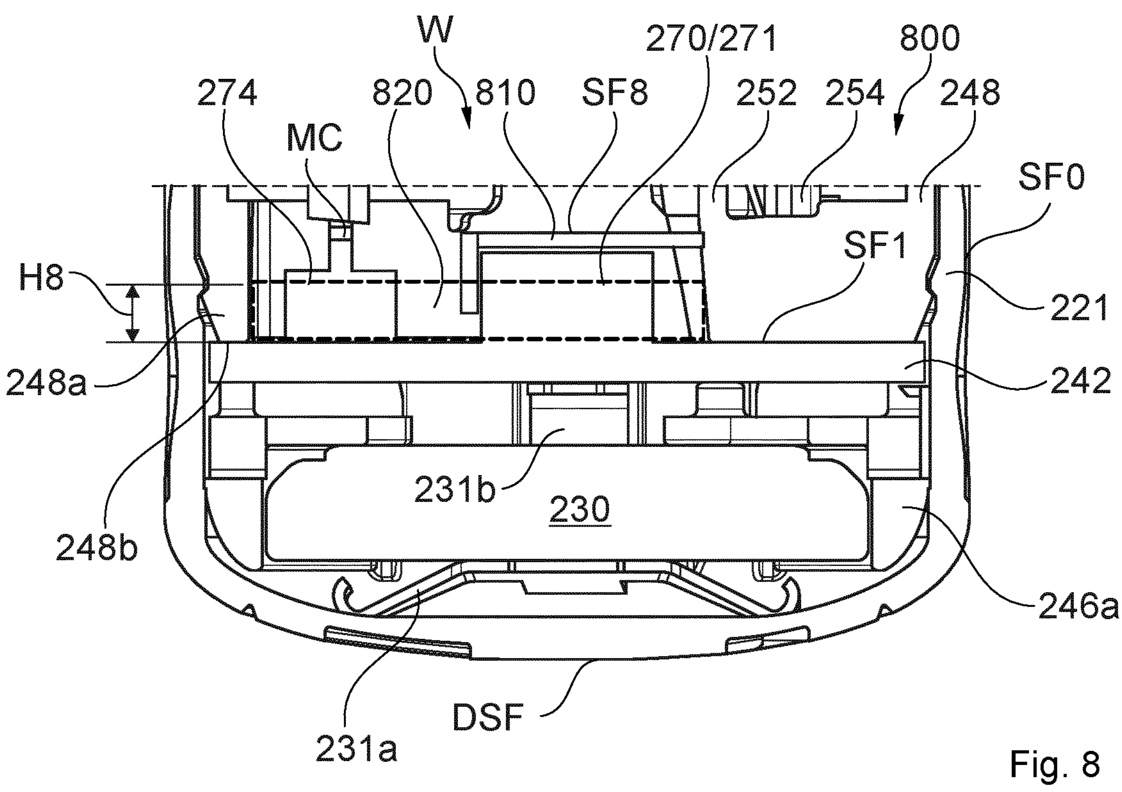

In the examples according to FIGS. 6 to 8, module part is a chassis comprising a tubular wall portion 248*a* which is arranged only on one side of the circuit carrier 242. More specifically, a proximal end portion 248*b* of wall portion 248*a* is adjacent to circuit carrier 242. A further chassis part is arranged on the opposite side of the circuit carrier 242. The further chassis comprises a separate tubular wall portion 246*a* which carries the battery/accumulator 230.

Furthermore, the example illustrated in FIG. 2 comprises a separate lid 224 which is separate from a housing 221 of the electronic module 220. Contrary, in FIGS. 6 to 9, a housing 221 is used which has an integral delivery surface DSF, e.g., no separate lid 224 is used. Housing 221 may also comprise or include integrally an adapter element similar to adapter 210 mentioned above, e.g., an adapter element which allows fastening to the setting knob of a drug delivery device 100.

However, the same methods, especially with regard to the sealing of the electronic components, may be applied also for the example illustrated in FIGS. 1 to 5. However, these design details are independent from the potting (filling) method used to provide a potting compound 282 or a filling layer 620, 720, 820, 920.

FIG. 6 illustrates a method step during the manufacturing of an electronic module 600 of the modular system 98 according to a first filling embodiment using highly viscous filling material of a filling layer 620.

The following parts are illustrated in all four FIGS. 6 to 9:

- Component 270 may be a transmitter (send), for instance a Bluetooth® transmitter, or a receiver 272, for instance a Bluetooth® receiver. Component 270, 271, 272 is named as a second electrically operable component in the claims.
- Alternatively for or additionally to component 270, a component 271, for instance a capacitor 271 may be used. Component 271 is also named as second electrically operable component in the claims.
- Switch 274 which is named as a first electrically operable component in the claims and which may comprise a movable component MC,
- Battery 230, for instance a button cell or coin cell. A diameter of battery 230 may be less than 2 cm (centimeter) or less than 1.5 cm. Alternatively, a rechargeable accumulator may be used or another energy source.
- A first contact 231*a* of battery 230/accumulator (plus pole, plus potential, positive terminal),
- A second contact 231*b* of battery 230/accumulator (minus pole, negative terminal, negative potential, ground),
- Optical guide 254 or corresponding optical guides 254*a*, 258*a*, 254*b*, 258*b*,
- Wall 252, and
- Annular wall 248.

However, further parts may also be provided in the examples illustrated in FIGS. 6 to 9:

- optional keying features K1*a*, K2*a*; K2*a*, K2*b*, and/or
- optional hooks 320, 322, 324; 420, 422, 424, and/or
- optional clip connections 326*a*, 326*b*; 426*a*, 426*b*, etc.

A setting surface SF0 is directed radially outwards and may extend circumferentially around housing 221 of electronic module 600, 700, 800 and 900.

Electronic module 600 may comprise a second electrically operable component of the circuitry, for instance at least one of components 270, 271 and/or 272. The first component, for instance switch 274, may have a first construction height H6*c* measured from the component surface SF1. The first construction height H6*c* may be different from a maximum construction height of the first component. Thus, the maximum construction height may extend from a bottom of a housing of switch 274 up to the free end of a button of switch 274, see movable component MC. The first construction height H6*c* may correspond to the height of the housing of switch 274. If the first component is an electro-optical component, for instance an LED (light emitting diode) or a multi-color LED IC (integrated circuit), the first height H6*c* may extend to a reference point on the housing of the LED or to the top edge of a housing of the LED integrated circuit. The maximum construction height of the LED or of the LED IC may be more than the first construction height and may include for instance an optical lens of the LED or of the LED IC.

The second component 270, 271 and/or 272, may have a second construction height H6*d* measured from the component surface SF1. The second construction height H6*d* may correspond to a maximum construction height of second component 270, 271 and/or 272 or may be less than a maximum construction height of second component 270, 271 and/or 272.

The first construction height H6*c* may also be valid for first component 274, for instance switch, in electronic modules 700, 800 and 900, see FIGS. 7 to 9 which are explained in more detail below. Similarly, the second construction height H6*d* may also be valid for second component 270 and/or 271 and/or 272, for instance transmitter or capacitor, in electronic modules 700, 800 and 900, see FIGS. 7 to 9.

The second construction height H6*d* may be greater than the first construction height H6*c*, for instance by one of the amounts mentioned in the first part of the description above. The first electrically operable component 274 may be embedded into filling layer 620 at most to the first construction height H6*c*. Second electrically operable component 270 and/or 271 and/or 272 may be embedded into filling layer 620 at least up to the second construction height H6*d* or up to a third height which is greater than first construction height H6*c* but less than second construction height H6*d*. Thus, second electrically operable component 270 and/or 271 and/or 272 may also be covered by filling layer 620, e.g., material of filling layer 620 may also extend above the top surface of second electrically operable component 270 and/or 271 and/or 272.

Filling layer 620 may comprise a first profile in a first cross section which is perpendicular to component surface SF1 and which may correspond to the plane which is illustrated in FIG. 6. In the first cross section the thickness of filling layer 620 may be less in the two peripheral regions or in at least one peripheral region, see for instance thickness H6*b*, compared to the thickness H6*a* in a central region. First electrically operable component, for instance switch 274 may be arranged in one of the peripheral regions, see left side in FIG. 6. Further, preferably, filling layer 620 may comprise a second profile in a second cross section which is perpendicular to the component surface and perpendicular to the first cross section. In the second cross section the thickness of filling layer 620 may also be less in the two peripheral regions or in at least one peripheral region compared to the thickness of filling layer 620 in a central region, see for instance thickness H6*a*.

Thus, a well W is formed of wall portion 248*a* and circuit carrier 242. Well W is used to accommodate liquid or viscous filling material of filling layer 620 which may be poured into well W in a central region, see arrow 610 or in another appropriate region. Fast hardening of the filling material may result in the profiles of filling layer 620 mentioned above, e.g., there may be a first slope G1 of the free surface of filling layer 620 from the right side to a central region and a second slope G2 of the free surface of filling layer 620 from the left side to the central region. Slopes G1 and G2 may be the same or may be different from each other. Slope G1 may include an angle A6*b* with surface SF1. Slope G2 may include an angle A6*a* with surface SF1. Angle A6*b* and/or A6*a* may be in the range of 5 degrees to 30 degrees to give only one example.

A material with high viscosity may be used, e.g., with a viscosity of more than 10, more than 100 or more than 1000 or more than 10000 mPa*s (milli Pascal second) (cP Centipoise). The viscosity may be less than 10^10 mPa*s (Cp) or less than 10^12 mPa*s (Cp) to give only some examples. These values are valid for a temperature of 20° C. (degrees Celsius). The viscosity may be lower if temperature is higher.

An automatic filling machine may be used to fill filling material of filling layer 620 into well W. Alternatively, a syringe may be used to fill filling material manually into well W. Assembled module 600 or partially assembled module 600 (for instance without battery 230, housing 221, and/or wall portion 246*a*) may be filled with filling material of filling layer 620.

FIG. 7 illustrates a method step during the manufacturing of an electronic module 700 of the modular system 98 according to a second filling embodiment using a conformal coating layer 710 applied for instance by conformal coating prior to filling.

A further sealing element, e.g., a coating layer 710, may be used in addition to a filling layer 720. Second electrically operable component 270 and/or 271 and/or 272 may comprise the coating layer 710 on the surface which is farthest away from circuit carrier 242 and at least partially also on its side surfaces, see FIG. 7, left side surface and right side surface. Coating layer 710 may extend to filling layer 720 and/or may be in contact with the filling layer 620.

Coating layer 710 may comprise or may consist of a coating material. The coating material may comprise or may consist of silicone. A spray or a liquid may be used to apply coating layer 710 to second component 270 and/or 271 and/or 272 before mounting of component 270 and/or 271 and/or 272 onto circuit carrier 242 or after mounting. If coating layer 710 is applied after mounting of second component 270/271 to circuit carrier 242 movable part MC may be covered with a protection structure in order to prevent that the coating material of coating layer 710 reaches movable parts and blocks movement thereof. MasterBond® UV 10-Med is an example for a spray which may be used. Other sprays or liquids may be used as well, especially materials which fulfill ISO (International Standardization Organization) 10993.

After assembling of circuit carrier 242 and wall portion 248*a*, e.g., after forming well W, filling material of filling layer 720 may be filled into well W. The resulting filling layer 720 may have a constant thickness H7 across circuit carrier 242. Thickness H7 may be equal to or less than first height H6*c* of first component 274. Assembled module 700 or partially assembled module 700 (for instance without battery 230, housing 221, and/or wall portion 246*a*) may be filled with material of filling layer 720. Second component 270/271 is sealed by coating layer 710 and by material of filling layer 720. Second component 270/271 may be embedded into the material of filling layer 720 only to a height which is equal to the first height H6*c* or less than the first height H6*c*.

Again, an automatic filling machine may be used to fill filling material of filling layer 720 into well W. Alternatively, a syringe may be used to fill filling material manually into well W. Viscosity of the filling material of filing layer 720 may be lower compared to the embodiment of FIG. 6, for instance less than 10 mPa*s (milli Pascal second) at 20° C. (degrees Celsius).

FIG. 8 illustrates a method step during the manufacturing of an electronic module 800 of the modular system 98 according to a third filling embodiment using an additional cover 810, preferably an integral cover 810 of a chassis 222

(module part in the claims) which comprises also wall portion 248 and/or 248*a* and/or 252.

Integral cover 810 or a cover which is separate from chassis 222 (module part in the claims) and/or from wall portion 248 and/or wall portion 248*a* may be used as an additional sealing element for second component 270 and/or 271 and/or 272. Second component 270 and/or 271 and/or 272 may be sealed by the integral cover 810 and by the filling layer 820 into which the integral cover 810 may be embedded at least partially. Second component 270/271 may be embedded into the material of filling layer 720 only to a height which is equal to the first height H6*c* or less than the first height H6*c*.

Integral cover 810 may comprises at least one flat surface SF8 on a top cover wall. Flat surface SF8 may comprise a marking and/or carry a label. A laser marking may be used which is branded and/or melted into the material on surface SF8, for instance into a plastic material.

There may be three side walls of cover 810 which surround second component 270, 271 and/or 272. One of these three side walls is illustrated in FIG. 8 on the right side of component 270/271. A fourth sidewall may be formed by wall portion 248. Alternatively, a fourth side wall may be connected with wall portion 248, for instance via a supporting structure. The height of the side walls of cover 810 may be less than the height of sidewalls of component 270/271/272, for instance in order to use less material for cover 810. Alternatively, the height of side walls of cover 810 may be the same or more than the height of sidewalls of component 270/271. The lower ends of the side walls of cover 810 are embedded into filling layer 820 and/or may made contact to filling layer 820, e.g., on its outer surfaces.

After assembling circuit carrier 242 and wall portion 248*a*, e.g., after forming well W, filling material of filling layer 820 may be filled into well W. The resulting filling layer 820 may have a constant thickness H8 across circuit carrier 242. Thickness H8 may be equal to or less than first height H6*c* of first component 274. Assembled module 800 or partially assembled module 800 (for instance without battery 230, housing 221, and/or wall portion 246*a*) may be filled with the filling material of filling layer 820.

An automatic filling machine may be used to fill filling material of filling layer 820 into well W. Alternatively, a syringe may be used to fill filling material manually into well W. Viscosity of the filling material of filling layer 820 may be lower compared to the embodiment of FIG. 6, for instance less than 10 mPa*s (milli Pascal second) at 20° C. (degrees Celsius).

Figure 9:
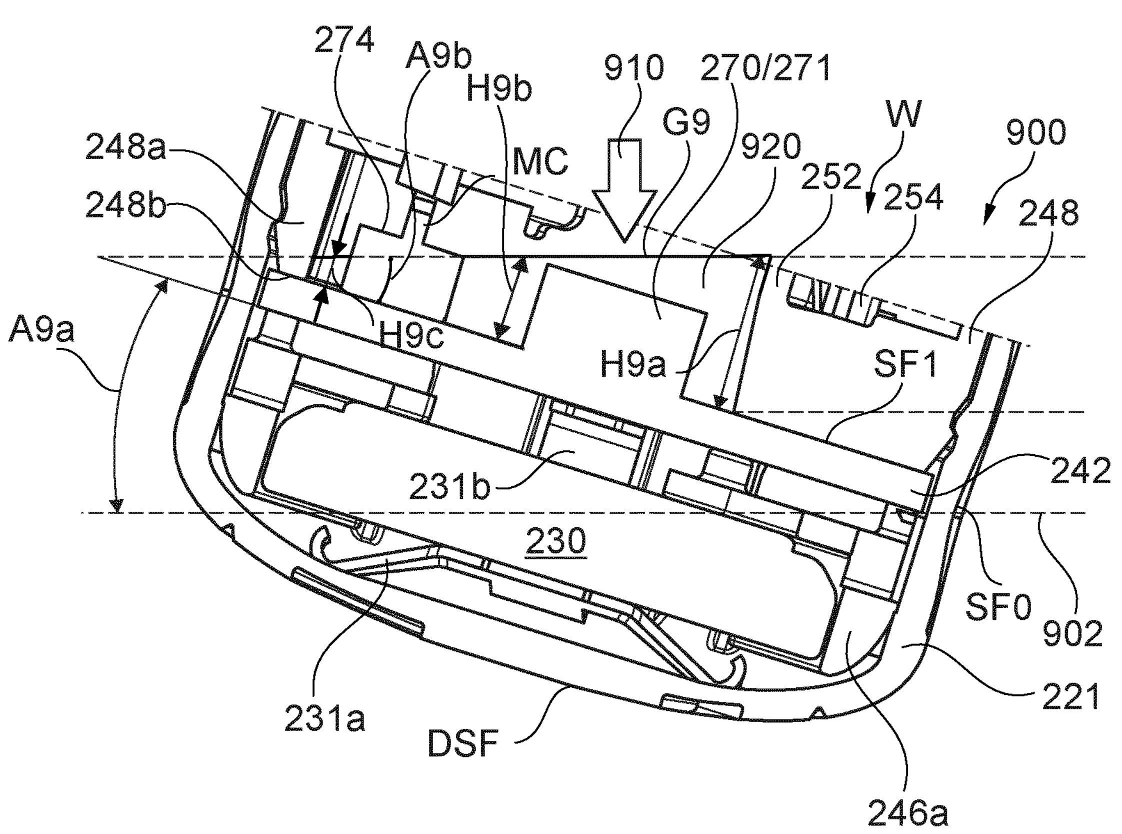

FIG. 9 illustrates a method step during the manufacturing of an electronic module 900 of modular system 98 according to a fourth filling embodiment with inclination of the electronic module 900 during filling in material of filling layer 920 into a well W.

Filling layer 920 may comprise a first profile in a first cross section which is perpendicular to the component surface SF1 and which may correspond to the plane which is illustrated in FIG. 9. In the first cross section, the thickness of the filling layer 920 may increase, preferably continuously, from a first thickness H9*c* in a first one of the peripheral regions to a second thickness H9*b* in a central region and further to a third thickness H9*a* in a second one of the peripheral regions. First electrically operable component 274 may be arranged in the first one of the peripheral regions. First thickness H9*c* of filling layer 920 may be equal to or less than first height H6*c* of first component 274. Therefore, a movable component MC of first component 274 is not covered by filling layer 920.

Filling layer 920 may comprises or may have a second profile in a second cross section which is perpendicular to the component surface SF1 and perpendicular to the first cross section. In the second cross section, the thickness of filling layer 920 may be constant or may deviate only by at most two percent from a maximum filling height or thickness H9*a* of filling layer 920. The second cross section may also extent through peripheral portions and through a central region.

Filling layer 920 may comprise a free surface which is the result of casting or pouring the filling material 920 to the circuit carrier using an inclination angle A9*a*, A9*b* of circuit carrier 242 and/or well W and/or of module 920 with regard to a horizontal plane 902. Inclination angle A9*a*, A9*b* may be at least 5 degree, at least 10 degree or at least 15 degree.

Assembled module 900 or partially assembled module 900 (for instance without battery 230, housing 221, and/or wall portion 246*a*) is tilted as illustrated in FIG. 9. Thereafter, liquid filling material is filled into well W, for instance in a central portion, see arrow 910, or into another appropriate portion.

There may be only one continuously slope G9 between a free surface of filling layer 920, e.g., a surface which is not covered or adjacent to other parts, and component surface SF1. Slope G9 corresponds to inclination angle A9*a*, A9*b* which was used during filling of well W with filling material of filling layer 920.

There may be the following method steps in all examples mentioned above (FIGS. 2, 6, 7, 8 and 9):

- Assembling circuit carrier 242 and wall portion 248*a*, e.g., forming well W,
- Tilting the assembly or the pre-assembly (only in the example of FIG. 9),
- Filling material of filling layer 282, 620, 720, 820, 920 may be filled into well W,
- Optionally, using temper steps to harden the filling material of filling layer 282, 620, 720, 820, 920 compared to waiting only until filling layer is solid,
- Optionally performing further assembling steps of module 120, 220, 600, 700, 800 or 900.

An automatic filling machine may be used to fill filling material of filling layer 920 into well W. Alternatively, a syringe may be used to fill filling material manually into well W. Viscosity of filling material of filling layer may be lower compared to the embodiment of FIG. 6, for instance less than 10 mPa*s (milli Pascal second) at 20° C. (degrees Celsius, centigrade).

In all four embodiments, modules 600, 700, 800, 900 may be connected to medical drug delivery devices 100 in order to monitor setting of a dose and/or delivery of a set dose of medicament or drug Dr into the body of a patient.

Spoken with other words one part of the disclosure relates to light pipe/guide 254 or optical pipe protection, preferably against loads. The optical pipe may be an optical fiber, a tube or other optical guiding means. An additional coating 256 on the outer surface of the light pipe may be used to prevent damage from loads coming from outside to the light pipe. One option would be a metal coating or a similar robust material coating to stiffen up the structure of the light pipe. A second option would be a soft coating to absorb impact loads resulting in less stresses of the light pipe. Another option would be reinforced coatings e.g., carbon fiber reinforced polymer (in German language: CFK) filled materials. A combination of two or of three of these options is possible as well.

A second part of the disclosure relates to features that are used to protect a re-usable clip-on e-module (electronic module 120, 220, 600 to 900) from damage, dirt and water ingress, and of other environmental influences. The second part of the disclosure describes features used to protect a re-usable clip-on e-module 120, 220 from damage, dirt and water ingress, etc. The embodiments in this document are illustrated with the optical add-on module 120, 220, 600 to 900 for a disposable injection device, but are applicable to any module 120, 220, 600 to 900 attaching to an injection device. This document does not include a full description of the disposable device mechanism itself, nor of the optical add-on module.

The described methods are intended to be applicable within the context (e.g., size, cost, usability etc.) of the add-on module 120, 220, 600 to 900.

The second part of the disclosure relates to features of an add-on module that may be attached to a suitably configured pen injector for the purpose of recording doses that are delivered from the pen. The e-module 120, 220, 600 to 900 may be used as a memory aid and for accurate dose history logging. It may be envisaged that the e-module 120, 220, 600 to 900 could be configured to be connectable to a mobile device, or similar, to enable the dose history to be downloaded from the module on a periodic basis. This information may be used by the end-user, healthcare provider, or for research on a wider scale. Furthermore, the e-module 120, 220, 600 to 900 may be used to remind the user to change the drug delivery device that is connected to the e-module 120, 220, 600 to 900 if the number of dose delivery operations is exceeded or reached for which the drug delivery device was designed.

A re-usable e-module 120, 220, 600 to 900 such as the proposed optical encoder, may be operable across a number of disposable devices and may be resistant to physical damage and ingress of dirt and water when not attached to a drug delivery device. The features described in the second part of the disclosure seek to variously minimise risk of damage to the encoder in such conditions.

Method 1—Physical Blocking Feature

It may be possible to utilise a blocking feature molded as part of the 'light pipe chassis', see 222 in FIG. 2, component as shown in FIGS. 3 and 4. FIGS. 3 and 4 show blocking ribs K1*a*, K2*a* and corresponding apertures K1*b*, K2*b* in button 108*a*, 108*b*. In this way, when assembled with the grip ring (for instance 210 in FIG. 2) and end cap (for instance casing or housing 221 shown in FIG. 2) components, a user would be unable to contact light pipes 254*a*, 258*a*, 254*b*, 258*b* or the electronic PCBA once the electronic module 120, 220 of modular system 300, 400 is assembled. A corresponding aperture in the button top surface of button 108*a*, 108*b* may be required as shown in FIGS. 3 and 4.

This method may have the advantage of not requiring any additional components, by using the light pipe chassis moulding itself to form blocking feature K1*a*, K2*a*, see 222 in FIG. 2. This blocking feature K1*a*, K2*a* may also act as a mechanical 'dedication' or keying feature.

Alternatively, this blocking feature K1*a*, K2*a* could be formed on a separate component which is clipped to the underside of light pipe chassis see 222 in FIG. 2. This may allow provision of more robust blocking feature blocking feature K1*a*, K2*a* and the possibility to form a water-tight seal to prevent water ingress to the PCBA.

Method 2—Elastomeric Potting Compound

Targeted at prevention of water and dust ingress, an elastomeric 'potting' compound 282 or a filling layer 620 to 920, such as silicone or polyurethane, may be applied to the underside of light pipe chassis 222, following assembly of the e-module 120, 220, 600 to 900, see FIG. 2. Potting compound 282 may be applied to the underside of re-usable clip-on e-module 120, 220, 600 to 900. Potting compound 282, 620 to 920 may be applied between filling height 280 and substrate 242.

The preferably low durometer (e.g., lower than durometer of chassis 222 or lower than Shore hardness of A80 or A75, and/or Dymax MD 1072-M (Shore hardness A70)) potting compound 282 may be applied directly onto the PCBA, and therefore may have good stress relief properties for fragile componentry on the board, e.g., resistors, capacitors, inductors and/or microprocessor or microcontroller. However, potting compound 282 may be sufficiently viscous in its melted state to prevent leakage through gaps.

With a potting compound 282 or filling layer 620 to 920 applied in this manner, ingress of dust and water to the conductive areas of the PCBA will be prevented.

If the potting compound 282 is filled to the level 280 as shown in FIG. 2 the micro-switch 274 will be proud of the compound and able to be operated by the switcher arm or pin. Additionally, the optical sensor(s) may kept isolated from the potted area, as the PCBA may be biased axially onto light pipe chassis 222, to form a barrier to potting compound 282 reaching the optically sensitive area of the optical sensor(s) 266 and/or optical radiation (light) source(s) 264. Filled to this level 280, potting compound 282 may be prevented from contacting optical sensor(s) 266 and/or optical radiation source(s) 264 by features 252 (wall), 260 (rib), etc.

Methods 1 and 2 may also be combined.

Elastomeric Potting Variants

The elastomeric potting could be applied to the electronic module 120, 220, 600 to 900 in a number of ways, seeking to cover all electronic components, with the exception of the exposed switch 274 or micro-switch for example. The micro-switch 274 may be at a lower height than the other components, but is not required to be covered with potting compound 282 and/or filling layer 620 to 920, as this would prevent reliable function of the micro-switch 274.

Variant 2a—Application of Potting Compound or Encapsulant Over Tallest Components (FIG. 6)

In this variant, the micro-switch 274 height is below that of other nearby electronic components (e.g., capacitor(s)). The elastomeric potting is selected to be highly viscous or sufficiently viscous, and is applied for instance directly above the tallest components. In such an arrangement, the potting compound 282 may be cured (e.g., using UV (ultra violet) irradiation) to ensure that the potting compound 282/filling material 620, 720, 820, 920 sets before rising to the level of the micro-switch 274.

This concept allows the micro-switch 274 or another mechanical, electromechanical or optoelectronic component to remain exposed, while covering the surrounding electronic components fully or to a larger degree compared to e.g., the micro switch 274. An elastomeric potting max be applied directly above the tallest component, see arrow 610 in FIG. 6 which illustrates the application of potting compound above tallest components. An encapsulant may be used instead of a potting compound, to the same effect.

Variant 2b—Application of Conformal Coating Prior to Potting (FIG. 7)

In this variant, the micro-switch 274 height or the height of another comparably shallow component is again below that of other nearby electronic components (e.g., capacitor(s), Bluetooth® modules). A conformal coating (e.g., silicone spray such as MasterBond® UV10-MED) or a non-conformal coating may be applied to the tallest components on the board and cured prior to the application of the elastomeric potting or filling material 720. The potting material may be filled up to a height below the critical height on the micro-switch. Isolation of the tall electronic components from water and dust ingress is therefore ensured by means of the conformal or non-conformal coating. FIG. 7 illustrates the application of conformal coating to tallest components prior to potting.

Variant 2c—Use of an Integral 'Cover' for Tallest Components (FIG. 8)

In this variant, the micro-switch 274 height or the height of another component is again below that of other nearby electronic components (e.g., capacitor(s)). A 'cover' feature 810 may be formed on the Light Pipe Chassis component 222. This component or feature 810 may prevent physical contact from the underside with the tallest components. Elastomeric potting 282 or other filling material 820 may be applied surrounding this cover feature 810, forming a seal. This method allows potting compound 282 or filling layer 820 to be applied to a lower level, meaning that the micro-switch 284 or other component can remain exposed while the tallest components are protected from water and dust ingress. This integral cover 810 may also provide a flat surface SF8 for laser marking or labelling, if required. FIG. 8 illustrates a cover component/feature 810 used to prevent contact with tallest components. A capacitor cover which is integral to light pipe chassis 222 may be used.

Variant 2d—Tilting of Module to Control Potting Height (FIG. 9)

In this variant, the micro-switch 274 or other component height is again below that of other nearby electronic components (e.g., Capacitors). The module 120, 220, 900 is therefore held at a tilted angle, relative to horizontal, so that the level of the elastomeric potting 282 or other filling material 920 when applied is at a non-zero angle A9*a*, A9*b* relative to the PCB 242. This method allows the taller components to be covered, while leaving the micro-switch 274 or another component exposed. FIG. 9 illustrates module 120, 220 held at an angle A9*a*, A9*b* to the horizontal during potting application, e.g., potting is applied when the module is held at an angle A9*a*, A9*b*, see arrow 910.

The concept described within the second part of the disclosure is believed to be the use of blocking and/or ingress prevention features as applied to a re-usable clip-on encoder or electronic module 120, 220. This document has shown specifically useful implementations of the second part of the disclosure. In the broadest generic terms, this second part of the disclosure as well as all other parts of the disclosure may be applicable to any injector device 100 where a reusable electronic module 120, 220, 600 to 900 is to be attached and removed.

A third part of the disclosure relates to a delivered dose recording in an injection device 100, using for instance an optical add-on e-module 120, 220, 600 to 900. The third part of the disclosure describes recording doses that are delivered from injection device 100. It may be applicable to drug delivery devices where the number sleeve and/or the dial sleeve may rotate relative to dose button 108, 108*a*, 108*b* during injection but may not rotate relative to that component during dialing. Alternatively, recording of doses may be performed during dialing, e.g., rotation of the number sleeve and/or the dial sleeve may be determined. The embodiments in this document are illustrated with a specific disposable injection device 100 but are also applicable to other drug delivery devices, for instance to any device with the indicated component movements. This document does not include a full description of the (disposable) drug delivery device mechanism itself. The injection device 100 may be required to be adapted to provide axial access through the dose button or another button 108 for a preferably flexible switch element and/or one or more 'light pipes', in addition to retention features for the electronic module add-on. The electronic module 120, 220, 600 to 900 add-on may comprise a 'light pipe chassis' 222 which may be a single optically transparent plastic molding comprising one or more light pipes or optical guides 254 to facilitate optical sensing of for instance a castellated top surface of the number sleeve component and/or the dial sleeve component or of a clutch element that is inserted into the dial sleeve component. The dial sleeve component or element may extend more and more out of the chassis during dialing with greater set doses depending on the selected dose. Additionally, this 'light pipe chassis' 222 may comprise a flexible or rigid element to trigger micro switch 274 or another appropriate switch element to indicate axial mode-shift when the dose button or another button (release) is depressed to deliver a dose. The electronics may be mounted within the 'light pipe chassis' 222 which may then be covered by an 'Over-cap' 221, 210.

The relative rotation between the dose button and the number sleeve and/or dial sleeve and/or clutch within dial sleeve may be encoded optically using for instance an incremental encoder (for example, a quadrature encoder) with for instance two reflective sensors 254, e.g., IR (infrared) sensors, looking axially at castellations on the top surface of the number sleeve and/or dial sleeve and/or clutch within dial sleeve.

A quadrature encoder may be an incremental encoder with two out-of-phase output channels where sensing the direction of movement is required. Each channel may provide a specific number of equally spaced pulses per revolution (PPR) and the direction of motion may be detected by the phase relationship of one channel leading or trailing the other channel.

Also the third part of the disclosure relates to features of an add-on e-module 120, 220, 600 to 900 that may be added to a suitably configured pen injector for the purpose of recording doses that are delivered from the pen. This functionality may be of value to a wide variety of device users as a memory aid or to support detailed logging of dose history. It may be envisaged that e-module 120, 220, 600 to 900 may be configured to be connectable to a mobile device, e.g., smart phone, or similar, to enable the dose history to be downloaded from the module on a periodic basis. Furthermore, the e-module 120, 220, 600 to 900 may be used to remind the user to change the drug delivery device that is connected to e-module 120, 220, 600 to 900 if the number of dose delivery operations is exceeded or reached for which the drug delivery device 100 was designed.

Disclosed is an electronic module 120, 220, 600 to 900 add-on device which may be attached to a suitably configured disposable pen injector. The add-on device may allow the recording of dose history information, without the requirement to dispose of high value electronics each time a new injection pen is required, and with minimal changes to the existing core mechanism of a disposable or non-disposable injector.

The (disposable) button may be embodied with axial retention bump features on the outer surface, to facilitate retention of add-on electronic module 120, 220, 600 to 900. Additionally, there may be an annular groove in the top surface, with for instance with only one aperture or with more than one aperture, e.g., four apertures, to allow access through the dose button or other button (e.g., release button of an autoinjector) to the number sleeve and/or to the dial sleeve and/or to a clutch element within the dial sleeve beneath.

The number sleeve and/or the dial sleeve and/or the clutch element within the dial sleeve may be embodied with for instance 24 clutch teeth which may engage with the dose button or with another part at the proximal end of the drug delivery device. These clutch teeth or other indicator features may be castellated features which may be arranged at the distal end of the light pipe or optical guide 254, 254*a*, 258*a*, etc. and whose rotation can be encoded to record delivered dose size of drug Dr.

Dose button and/or release button may be designed to bottom out on the number sleeve and/or on the dial sleeve and/or on the clutch element within the dial sleeve to ensure a small and repeatable axial distance between the light pipe or optical guide and the clutch teeth when the dose button or another button is depressed.

There may be the following components comprised within add-on electronic module 120, 220, 600 to 900:

- chassis 222 that may be coupled axially and rotationally to the dose button or another button or only to the casing of an autoinjector,
- PCB, electronic components and coin cell (housed within the chassis),
- an 'over cap' or casing 221, optionally in two part form comprising adapter element 210.

The 'over cap' may be used to retain and/or to house the electronics and/or to provide visual and tactile features for the user on its outside surfaces.

The embodiment of the 'Light pipe chassis' 222 that is shown in FIG. 2 may comprise two light pipes or optical guides 254, 254*a*, 254*b*, 258*a*, 258*b*, see also FIGS. 3 and 4, above which may be mounted reflective or transmissive optical sensors 266, e.g., IR sensors, illustrated in FIG. 2. These light pipes or optical guides 254, 254*a*, 254*b*, 258*a*, 258*b* may allow the optical sensor(s) 266 (e.g., mounted axially within the 'light pipe chassis' or chassis 222 at the proximal P end of the light pipes) to detect the presence or otherwise of castellation features at the distal D end of the light pipe or optical guide 254, 254*a*, 254*b*, 258*a*, 258*b* when the dose button or another button is pressed in. Alternative, an autoinjector may be used that does not comprise a release button but a needle shroud that releases the mechanism 106 if the drug delivery device 100 is pressed against an injection site.

When the dose button 108 or the dosing surface DSF is pressed and/or when the selected or delivered amount of drug Dr has to be determined, the distal end of the light pipe may be held at a small and well controlled axial distance from castellation features or other appropriate features. Additionally, the embodiment may comprise optionally a single flexible or rigid element, which will contact the top face of the number sleeve and/or of the dial sleeve or of another part of the drug delivery device when the dose button 108 or another button is pressed. Alternatively, a needle shroud may be used as trigger element. This flexible or rigid element may deflect or move to contact micro switch 274 or another switch mounted axially on the PCB within the 'light pipe chassis' and may serve as an axial mode-shift trigger, to wake up electronic module 120, 220, 600 to 900, especially a power unit of electronic module 120, 220. This flexible or rigid element may contact the micro switch 274 after a small axial travel, but may be able to accommodate significant over-travel beyond this trigger point.

The embodiment of the third part of the disclosure may comprise clip features, intended to act as axial retention features when the add-on electronic module 120, 220, 600 to 900 is assembled to the dose button 108, to another button of the pen injector or directly to the pen injector. The add-on electronic module 120, 220, 600 to 900 may be designed to assemble to the dose button 108 in a unique rotational orientation. Furthermore, the outer diameter of the 'light pipe chassis' or of chassis 222 or of another chassis or module part may have features into which the 'Over Cap' can be rotationally coupled, so that those components move together. It may be envisaged that the 'light pipe chassis' component may be molded in polycarbonate or a similar polymer which is transmissive to infra-red radiation or other optical radiation in the range of the wavelength of the optical sensors.

Two of the three parts of the disclosure or all three parts of the disclosure may be combined.

Although embodiments of the present disclosure and their advantages have been described in detail, it should be understood that various changes, substitutions and alterations can be made therein without departing from the spirit and scope of the disclosure as defined by the appended claims. For example, it will be readily understood by those skilled in the art that many of the features, functions, processes and methods described herein may be varied while remaining within the scope of the present disclosure. Moreover, the scope of the present application is not intended to be limited to the particular embodiments of the system, process, manufacture, method or steps described in the present disclosure. As one of ordinary skill in the art will readily appreciate from the disclosure of the present disclosure, systems, processes, manufacture, methods or steps presently existing or to be developed later that perform substantially the same function or achieve substantially the same result as the corresponding embodiments described herein may be utilized according to the present disclosure. Accordingly, the appended claims are intended to include within their scope such systems, processes, methods or steps. The embodiments mentioned in the first part of the description may be combined with each other. The embodiments of the description of Figures may also be combined with each other. Further, it is possible to combine embodiments mentioned in the first part of the description with examples of the second part of the description which relates to FIGS. 1 to 9.

The invention claimed is:

1. A modular system for a drug delivery device, the modular system comprising:

- a mechanical module that comprises a distal end, a proximal end, and a mechanism that is configured to set and/or deliver a dose of a drug out of the distal end of the mechanical module;
- an electronic module coupleable to the proximal end of the mechanical module, the electronic module comprising a detector unit for detecting an amount of drug arranged for delivery, an electronic unit that is operatively coupled to the detector unit, and a substrate that carries one or more parts of the electronic unit,
- wherein one or more sides of the substrate is covered at least partially by a potting compound, and
- wherein a chassis comprising a part of the detector unit is configured to separate the potting compound from an electrical sensor or from a radiation source of the detector unit.

2. The modular system according to claim 1, wherein the detector unit is coupled to an extension feature that extends from the electronic module distally beyond the proximal end of the mechanical module a distance of at least 3 mm.

3. The modular system according to claim 2, wherein the mechanical module comprises a proximal part with an aperture, wherein the extension feature extends into the aperture or to a position near the aperture, and optionally, wherein the position has a distance to the aperture in a range of approximately 0.1 mm to approximately 3 mm.

4. The modular system according to claim 3, wherein the proximal part is a casing, a grip button, or an extension sleeve of the mechanical module.

5. The modular system according to claim 2, wherein the chassis is configured to separate the potting compound from the extension feature of the detector unit.

6. The modular system according to claim 1, wherein the mechanical module comprises a movable indicator element that is coupled to the mechanism, wherein the part of the detector unit is arranged at the indicator element, and wherein the detector unit is configured to detect a movement of the indicator element to determine the amount of the dose of the drug arranged for delivery by the mechanism during a dose delivery operation.

7. The modular system according to claim 1, wherein the electronic module comprises:

a housing part that houses the chassis, wherein the chassis is a separate component from the housing part or is integral to the housing part.

8. An electronic module comprising:

a detector unit for detecting an amount of a drug arranged for delivery;

an electronic unit operatively coupled to the detector unit, wherein the electronic module is configured to be removably coupled to a proximal end region of a mechanical module;

a substrate that carries a part of the electronic unit, wherein one or more sides of the substrate is covered at least partially by a potting compound; and a chassis comprising a part of the detector unit and that is configured to separate the potting compound from an electrical sensor or from a radiation source of the detector unit.

9. The electronic module according to claim 8, wherein the mechanical module is a drug delivery device.

10. The electronic module according to claim 8, wherein the mechanical module is an injection pen or an autoinjector.

11. The electronic module according to claim 8, wherein the mechanical module comprises a mechanism that is configured to set and/or to deliver a dose of the drug out of a distal end of the mechanical module.

12. The electronic module according to claim 8, comprising a housing which houses the chassis.

13. An electronic module comprising:

a detector unit for detecting an amount of a drug arranged for delivery;

an electronic unit operatively coupled to the detector unit, wherein the electronic module is configured to be removably coupled to a proximal end region of a mechanical module;

a substrate that carries a part of the electronic unit, wherein one or more sides of the substrate is covered at least partially by a potting compound;

a chassis comprising a part of the detector unit and that is configured to separate the potting compound from an electrical sensor or from a radiation source of the detector unit;

a component surface of a circuit carrier, the component surface being formed by the substrate;

a first electrically operable component of a circuitry arranged on the component surface; and a side wall of the chassis, wherein the side wall is arranged adjacent to the circuit carrier, wherein the side wall and the circuit carrier cooperate to delimit a receiving space for a filling layer formed by the potting compound, and wherein the filling layer contacts one or more of the side wall, the first electrically operable component, and the component surface.

14. The electronic module according to claim 13, further comprising a second electrically operable component of the circuitry, wherein the first electrically operable component has a first construction height measured from the component surface, wherein the second electrically operable component has a second construction height measured from the component surface, wherein the second construction height is greater than the first construction height, wherein the first electrically operable component is embedded into the filling layer at most up to the first construction height, and wherein the second electrically operable component is embedded into the filling layer at least up to a third height that is greater than the first construction height.

15. The electronic module according to claim 14, wherein the second electrically operable component is embedded into the filling layer at least up to the second construction height or up to the third height, wherein the third height is less than the second construction height.

16. The electronic module according to claim 13, wherein the filling layer comprises:

a first profile in a first cross section that is perpendicular to the component surface, and a second profile in a second cross section that is perpendicular to the component surface and perpendicular to the first cross section, wherein a thickness of the filling layer of the first cross section is lower in two peripheral regions than in a central region of the first cross section, wherein the first electrically operable component is arranged in one of the two peripheral regions, and wherein a thickness of the filling layer of the second cross section is lower in two peripheral regions than in a central region of the second cross section.

17. The electronic module according to claim 13, wherein the filling layer comprises:

a first profile in a first cross section that is perpendicular to the component surface, and a second profile in a second cross section that is perpendicular to the component surface and perpendicular to the first cross section, wherein a thickness of the filling layer of the first cross section increases from a first thickness in a first peripheral region to a second thickness in a central region and to a third thickness in a second peripheral region, and wherein the first electrically operable component is arranged in the first peripheral region, wherein a thickness of the filling layer of the second cross section deviates from a maximum filling height of the filling layer by at most two percent.

18. The electronic module according to claim 13, comprising a second electrically operable component of the circuitry, wherein the first electrically operable component has a first construction height measured from the component surface, wherein the second electrically operable component has a second construction height measured from the component surface, wherein the second construction height is greater than the first construction height, wherein the first electrically operable component and/or the second electrically operable component is embedded into the filling layer at most to the first construction height, and wherein the second electrically operable component is sealed by a combination of the filling layer and a sealing element different from the filling layer.

19. The electronic module according to claim 18, wherein the sealing element is a coating layer, wherein the second electrically operable component comprises the coating layer on a surface furthest away from the circuit carrier and at least partially on one or more side surfaces, wherein the coating layer extends to the filling layer and/or is in contact with the filling layer, wherein the coating layer extends to the component surface and/or is in contact with the component surface.

20. The electronic module according to claim 18, wherein the sealing element is an integral cover for the second electrically operable component that is integral with a module part comprising at least one side wall, and wherein the second electrically operable component is sealed by the integral cover and by the filling layer, the integral cover being embedded at least partially in the filling layer.

21. The electronic module according to claim 20, wherein the integral cover comprises a flat surface comprising a marking and/or carrying a label.

22. The electronic module according to claim 8, wherein the electronic module comprises:

a module part comprising at least one side wall, and one or more of an electrical power source carried by the module part or by a mechanical carrier, a delivery button comprising a delivery surface configured to be pressed to initiate a delivery of a drug from a drug delivery device, the delivery button carried by the module part or by the mechanical carrier, and a lateral setting surface configured to set a dose of the drug for delivery.

* * * * *